United States Patent
Thompson

(10) Patent No.: US 6,185,454 B1
(45) Date of Patent: Feb. 6, 2001

(54) POWER CONSUMPTION REDUCTION IN MEDICAL DEVICES EMPLOYING JUST-IN-TIME VOLTAGE CONTROL

(75) Inventor: David L. Thompson, Fridley, MN (US)

(73) Assignee: Medtronic, Inc., Minneapolis, MN (US)

(*) Notice: Under 35 U.S.C. 154(b), the term of this patent shall be extended for 0 days.

(21) Appl. No.: 09/289,776

(22) Filed: Apr. 9, 1999

Related U.S. Application Data

(63) Continuation-in-part of application No. 09/067,881, filed on Apr. 29, 1998, now abandoned, and a continuation-in-part of application No. 09/181,460, filed on Oct. 28, 1998, and a continuation-in-part of application No. 09/181,459, filed on Oct. 28, 1998, and a continuation-in-part of application No. 09/181,517, filed on Oct. 28, 1998, and a continuation-in-part of application No. 09/181,523, filed on Oct. 28, 1998.

(51) Int. Cl.$^7$ .................................... A61N 1/36
(52) U.S. Cl. ........................................... 607/2
(58) Field of Search ........................ 607/2, 9, 4, 10; 257/237, 254, 257, 258, 263, 265, 292, 500

(56) References Cited

U.S. PATENT DOCUMENTS

| | | |
|---|---|---|
| 4,031,899 | 6/1977 | Renirie . |
| 4,428,378 | 1/1984 | Anderson et al. . |
| 4,460,835 | 7/1984 | Masuoka . |
| 4,561,442 | 12/1985 | Vollmann et al. . |
| 4,663,701 | 5/1987 | Stotts . |
| 4,791,318 | 12/1988 | Lewis et al. . |
| 4,791,935 | 12/1988 | Baudino et al. . |
| 5,022,395 | 6/1991 | Russie . |
| 5,052,388 | 10/1991 | Sivula et al. . |
| 5,154,170 | 10/1992 | Bennett et al. . |
| 5,185,535 | 2/1993 | Farb et al. . |
| 5,187,796 | 2/1993 | Wang et al. . |
| 5,292,343 | 3/1994 | Blanchette et al. . |
| 5,330,513 | 7/1994 | Nichols et al. . |
| 5,388,578 | 2/1995 | Yomtov et al. . |
| 5,447,519 | 9/1995 | Peterson . |
| 5,464,435 | 11/1995 | Neumann . |
| 5,496,351 | 3/1996 | Plicchi et al. . |
| 5,562,711 | 10/1996 | Yerich et al. . |
| 5,610,083 | 3/1997 | Chan et al. . |
| 5,683,432 | 11/1997 | Goedeke et al. . |
| 5,730,142 | 3/1998 | Sun et al. . |
| 5,778,881 | 7/1998 | Sun et al. . |
| 5,782,888 | 7/1998 | Sun et al. . |

OTHER PUBLICATIONS

Jan Mulder et al., "Application of the Back Gate in MOS Weak Inversion Translinear Circuits," IEEE Transactions on Circuits and Systems—I: Fundamental Theory and Applications, vol. 42, No. 11, Nov. 1995.

P–7739, Application of: Werner Peter Wohlgemuth, Serial No. 09/158,566, Filing Date, Sep. 22, 1998, "Cardiac Pacing System with Improved Physiological Event Classification Based on DSP".

P–3432 and P–3432 CIP, U.S. Patent Appln. Ser. Nos. 08/561,738 and 08/768,687 to Lambert Muhlenberg.

Primary Examiner—Scott M. Getzow
(74) Attorney, Agent, or Firm—Thomas F. Woods; Harold R. Patton; Girma Wolde-Michael

(57) ABSTRACT

Power consumption in medical and battery powered devices is reduced through the use and operation of a data monitor which measures, senses or detects signals, inputs or outputs in a medical device before they are input to a principal or main digital signal processor, controller or microprocessor. In response to detecting or measuring such a signal which meets certain amplitude, frequency and/or phase characteristics, the data monitor directs or controls voltage supply circuits to increase or decrease the voltages provided to certain circuits within the medical device. The voltages so employed are tailored to reduce the amount of power consumed by the medical device while preserving computational performance.

96 Claims, 20 Drawing Sheets

POWER CONSUMPTION REDUCTION IN MEDICAL DEVICES EMPLOYING JUST-IN-TIME VOLTAGE CONTROL

Claim to Priority and Reference to Related Application

This application is a Continuation-In-Part and claims priority and other benefits from the filing dates of the following patent applications: (1) U.S. patent application Ser. No. 09/067,881 for "Power Consumption Reduction in Medical Devices Using Multiple Supply Voltages and Clock Frequency Control" to Thompson, filed Apr. 29, 1998, and now abandoned; (2) U.S. patent application Ser. No. 09/181,460 for "Power Consumption Reduction in Medical Devices Employing Multiple Digital Signal Processors" to Thompson, filed Oct. 28, 1998; (3) U.S. patent application Ser. No. 09/181,459 for "Power Consumption Reduction in Medical Devices By Employing Different Supply Voltages" to Thompson, filed Oct. 28, 1998; (4) U.S. patent application Ser. No. 09/181,517 for "Power Consumption Reduction in Medical Devices Employing Multiple Supply Voltages and Clock Frequency Control" to Thompson, filed Oct. 28, 1998; and (5) U.S. patent application Ser. No. 09/181,523 for "Power Consumption Reduction in Medical Devices Employing Multiple Digital Signal Processors and Different Supply Voltages" to Thompson, filed Oct. 28, 1998, all hereby incorporated by reference herein in their respective entireties.

FIELD OF THE INVENTION

The present invention relates to the reduction of power consumption in integrated circuit designs, such as integrated circuits employed in medical devices, particularly implantable medical devices.

BACKGROUND OF THE INVENTION

Various devices require operation with low power consumption. For example, hand-held communication devices require such low power consumption and, in particular, implantable medical devices require low power capabilities. With respect to implantable medical devices, for example, microprocessor-based implantable cardiac devices, such as implantable pacemakers and defibrillators, are required to operate with a lower power consumption to increase battery life and device longevity.

Generally, such low power devices are designed using complementary metal oxide semiconductor (CMOS) technology. CMOS technology is generally used because such technology has the characteristic of substantially zero "static" power consumption.

Power consumption of CMOS circuits consists generally of two power consumption factors, namely "dynamic" power consumption and static power consumption. Static power consumption is only due to current leakage as the quiescent current of such circuits is zero. Dynamic power consumption is the dominant factor of power consumption for CMOS technology. Dynamic power consumption is basically due to the current required to charge internal and load capacitances during switching, i.e., the charging and discharging of such capacitances. Dynamic power (P) equals: $\frac{1}{2}CV_{DD}^2F$, where C is nodal capacitance, F is the clock or switching frequency, and $V_{DD}$ is the supply voltage for the CMOS circuit. As can be seen from the formula for calculating dynamic power (P), such dynamic power consumption of CMOS circuits is proportional to the square of the supply voltage ($V_{DD}$). In addition, dynamic power (P) is proportional to switching or clock frequency (F).

In accordance with the formula for dynamic power consumption, it has been effective in conventional CMOS integrated circuit designs to scale down the supply voltage for an entire device (e.g., hybrid) or integrated circuit (IC), i.e., operate the circuit at low supply voltages, to reduce power consumption for such designs. For example, in the MEDTRONIC SPECTRAX® device of circa 1979, IC circuitry was powered by one lithium iodine cell (as opposed to the two cells of the prior art). This reduced the supply voltage to 2.8 volts from 5.6 volts, thus reducing overhead current. Voltages required to be greater than 2.8 volts were generated by a voltage doubler, or alternatively by a charge pump (e.g., output pacing pulses). Further, for example, in the MEDTRONIC SYMBIOS® device of circa 1983, logic circuitry was powered by a voltage regulator controlling the IC supply voltage to a "sum of thresholds" supply. This regulator provided a supply to the IC (i.e., $V_{DD}$) of several hundred millivolts above the sum of the n-channel and p-channel thresholds of the CMOS transistors making up the IC. This regulator was self calibrating regarding manufacturing variations of the transistor thresholds.

Other devices have reduced power consumption in other manners. For example, various device designs have shut-down analog blocks and/or shut-off clocks to logic blocks not being used at particular times, thereby reducing power. Further, for example, microprocessor based devices have historically used a "burst clock" design to operate a microprocessor at a very high clock rate (e.g., generally 500–1000 Kilohertz (KHz)), for relatively short periods of time to gain the benefit of a "duty cycle" to reduce average current drain. A much lower frequency clock (e.g., generally 32 KHz) is used for other circuitry and/or the processor when not in the high clock rate mode, i.e., burst clock mode. Many known processor based implanted devices utilize the burst clock technique. For example, implanted devices available from Medtronic, Vitatron, Biotronic, ELA, Intermedics, Pacesetters, InControl, Cordis, CPI, etc., utilize burst clock techniques. A few illustrative examples which describe the use of a burst clock are provided in U.S. Pat. No. 4,561,442 to Vollmann et al., entitled "Implantable Cardiac Pacer With Discontinuous Microprocessor Programmable Anti Tachycardia Mechanisms and Patient Data Telemetry," issued Dec. 31, 1985; U.S. Pat. No. 5,022,395 to Russie, entitled "Implantable 25 Cardiac Device With Dual Clock Control of Microprocessor," issued Jun. 11, 1991; U.S. Pat. No. 5,388,578 to Yomtov et al., entitled "Improved Electrode System For Use With An Implantable Cardiac Patient Monitor," issued Feb. 14, 1995; and U.S. Pat. No. 5,154,170 to Bennett et al., entitled "Optimization for Rate Responsive Cardiac Pacemaker," issued Oct. 13, 1992.

FIG. 1 represents a graphical illustration of energy/delay versus supply voltage for CMOS circuits such as a CMOS inverter 10 shown in FIG. 2 for illustrative purposes. The inverter 10 is provided with a supply voltage, $V_{DD}$, which is connected to the source of a PMOS field effect transistor (FET) 12. PMOS FET 12 has its drain connected to the drain of an NMOS FET 14 whose source is connected to ground. In this configuration, an input $V_i$ applied to both the gates of FETs 12, 14 is inverted to provide output $V_o$. Simply stated, one clock cycle, or logic level change, is used to invert the input $V_i$ to $V_o$.

As shown in FIG. 1, the circuit logic delay increases drastically as the supply voltage is reduced to near one volt, as represented by delay line 16 and energy/delay line 18. As such, reducing of the supply voltage ($V_{DD}$) continuously to lower levels is impractical because of the need for higher supply voltages when higher frequency operation is required. For example, generally CMOS logic circuits must periodically provide functionality at a higher frequency, e.g., burst clock frequency. However, as the supply voltage ($V_{DD}$) is decreased, such energy consumption is reduced by the square of the supply voltage ($V_{DD}$) as is shown by energy consumption line 20. Therefore, speed requires a higher supply voltage ($V_{DD}$) which is in direct conflict with low power consumption.

Other problems are also evident when lower supply voltages ($V_{DD}$) are used for CMOS circuit designs. When a lower supply voltage is selected, static leakage current losses may arise, particularly at lower frequencies, due to increased static leakage current losses.

Various techniques for reducing power consumption in devices are known in the art, some examples of which may be found in at least some of the references listed in Table 1 below.

TABLE 1

| Patent No. | Inventor | Issue Date |
| --- | --- | --- |
| 4,031,899 | Renirie | 28 June 1977 |
| 4,460,835 | Masuoka | 17 July 1984 |
| 4,561,442 | Vollmann et al. | 31 December 1985 |
| 4,791,318 | Lewis et al. | 13 December 1988 |
| 5,022,395 | Russie | 11 June 1991 |
| 5,154,170 | Bennett et al. | 13 October, 1992 |
| 5,185,535 | Farb et al. | 9 February 1993 |
| 5,187,796 | Wang et al. | 16 February 1993 |
| 5,388,578 | Yomtov et al. | 14 February 199S |
| 5,610,083 | Chan et aI. | 11 March 1997 |

All references listed in Table 1 above are hereby incorporated by reference herein, each in its respective entirety. As those of ordinary skill in the art will appreciate readily upon reading the Summary of the Invention, Detailed Description of the Embodiments, and Claims set forth below, at least some of the devices and methods disclosed in the publications, patents or patent applications referenced in the present application, including those disclosed in the references listed in Table 1 above, may be modified advantageously in accordance with the teachings of the present invention.

SUMMARY OF THE INVENTION

The present invention has certain objects. That is, various embodiments of the present invention provide solutions to one or more problems existing in the prior art respecting circuitry design having lower power consumption, particularly with respect to implantable medical devices. Those problems include: CMOS, CML, SOS, SOI, BICMOS, PMOS and/or NMOS circuits having excessive dynamic power consumption which reduces battery life; the inability to utilize low voltage supply levels effectively; lack of ability to provide adequate processing capabilities such as high processing capabilities including telemetry uplink/downlink, morphology detection, initialization of devices, while still providing low processing capabilities such as sensing intrinsic beats, pacing, low speed telemetry, with the desired power consumption; and the inability to provide circuit designs that operate at lower frequencies and thus lower power consumption as opposed to the use of higher speed clocks such as burst clocks.

In comparison to known techniques for reducing power consumption in circuit designs, various embodiments of the present invention may provide one or more of the following advantages: reduced power consumption through the use of multiple digital signal processing (DSP) systems; reduced power consumption through the use of a lower voltage supply ($V_{DD}$); reduced power consumption by decreased clock frequency for circuit designs; increased longevity of circuits, particularly implantable device circuitry; provide a potential reduction in product size; providing high performance processing designs with additional features or functions due to the ability to reduce power with respect to other "required" features and functions; reduced static power consumption; providing multi-processor designs and DSP designs having additional features or functions due to the ability to reduce power with respect to other "required" features and functions; reduced current drain for an overall design, even when operating analog circuitry at higher supply voltages relative to the supply voltages applied to digital circuitry of the design.

Some embodiments of the invention include one or more of the following features: two or more digital signal processing systems; multiple processors, each performing functions at lower clock frequencies to reduce power consumption; a first and second digital signal processor operating on data representative of analog inputs to perform respective first and second functions at respective first and second clock frequencies during a predetermined time period with the first and second clock frequencies being such that the power consumed by the first and second digital signal processors during performance of such functions is less than the power that would be consumed if only one of the processors were to perform the functions within the time period; multiple digital signal processors having supply voltages that are reduced based on the reduction of clock frequency for such processors; providing analog inputs, e.g., cardiac sense signals, to the multiple processors for use in performing functions such as T-wave, P-wave, and R-wave detection; one or more analog circuits of a medical device (e.g., an atrial sense amplifier, a ventricular sense amplifier, a T-wave amplifier, one or more bandpass filters, one or more detection circuits, one or more sensor amplification circuits, one or more physiological signal amplification circuits, one or more output circuits, a battery monitor circuit, and/or a power on reset circuit) and one or more digital circuits of the medical device (e.g., a processor, a controller and/or a memory) with the supply voltage applied to the analog circuits being greater than that applied to the digital circuits; a source for applying a first fixed supply voltage to digital circuits of a medical device and a voltage generation circuit (e.g., a charge pump circuit) having the first fixed supply voltage applied thereto for generating a second fixed supply voltage to be applied to analog circuits of the medical device; adjustment of back gate bias of digital circuits of the medical device; level shifting of signals being communicated between analog circuits and digital circuits having different supply voltages applied thereto; employing various ones or combinations of the foregoing features in CMOS, CML (Current Mode Logic), SOS (Silicon on Sapphire), SOI (Silicon on Insulator), BICMOS, PMOS and/or NMOS circuitry.

DETAILED DESCRIPTION OF THE EMBODIMENTS

One embodiment of the present invention is first generally described in reference to FIGS. 3–15. More particularly, at least in part the use of multiple DSP systems to reduce power consumption is shown in those Figures.

Figure 1:
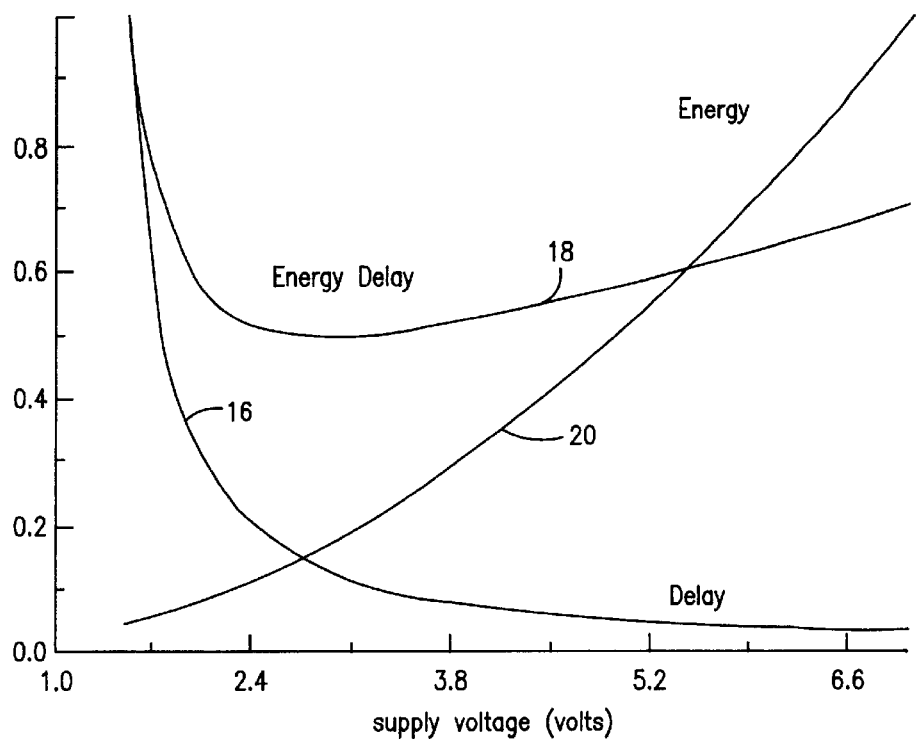
FIG. 1 is a graphical illustration showing energy/delay versus supply voltage for CMOS circuit operation.
Figure 2:
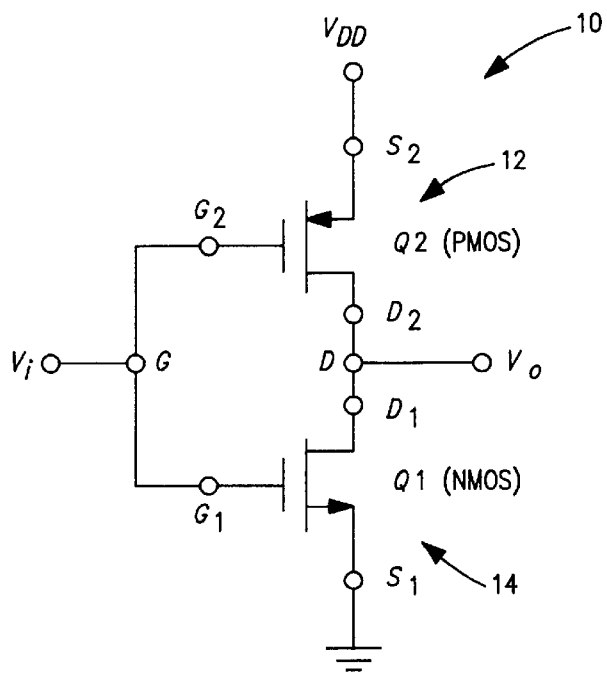
FIG. 2 shows a prior art CMOS inverter which is used as a building block in many CMOS circuit designs.
Figure 3:
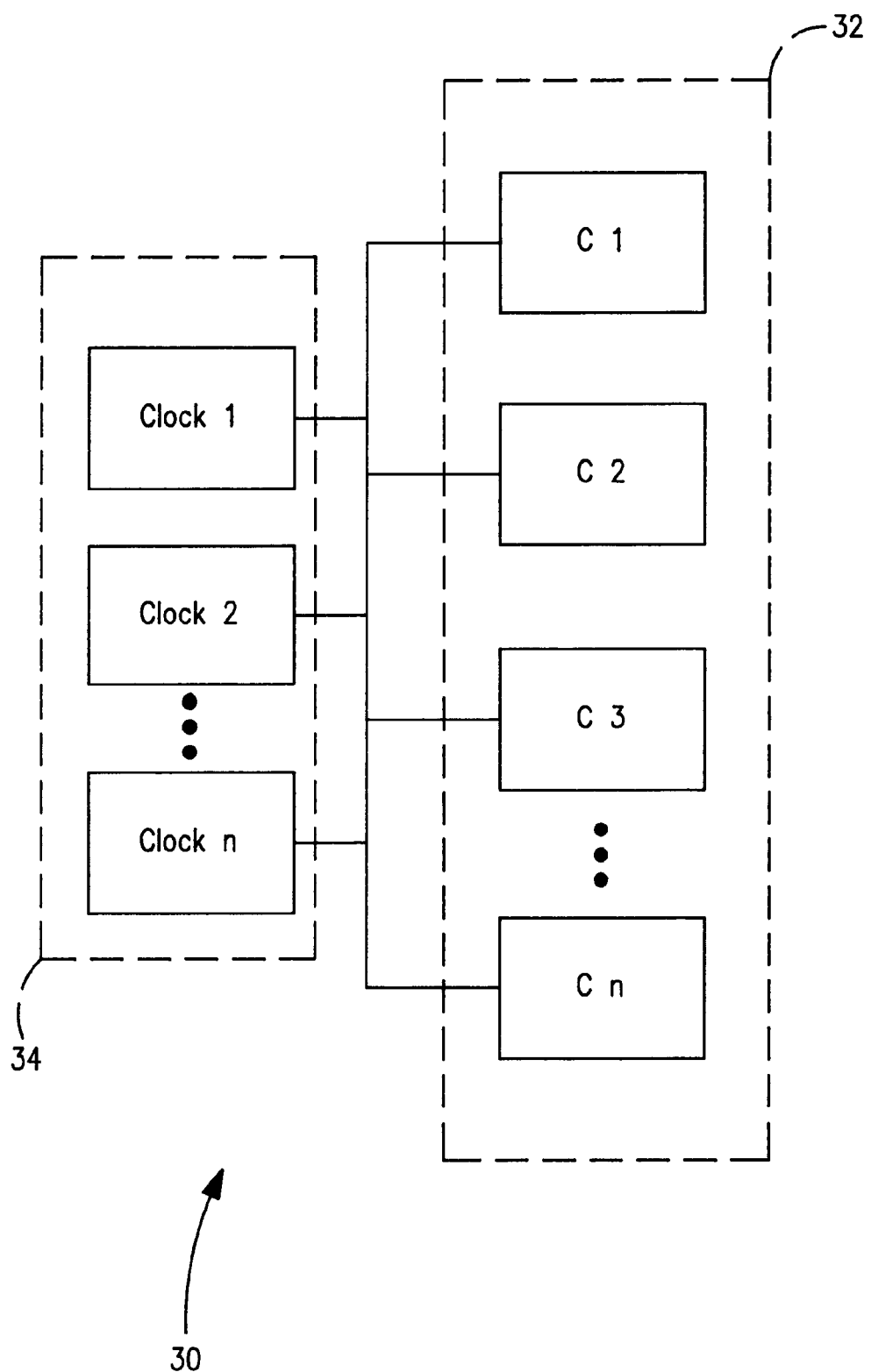
FIG. 3 is a block diagram of a just-in-time clocking system according to the present invention.

FIG. 3 shows a general block diagram of a just-in-time clock system 30. Just-in-time clock system 30 includes integrated circuit 32 and clock source 34. Integrated circuit 32 includes a plurality of circuits C1-Cn. Each circuit when operable is capable of performing one or more circuit functions. A function is defined herein as any operation performed on one or more inputs in a plurality of cycles that results in an output. Generally, the functions performed by the various circuits C1-Cn are usually, although not necessarily always, performed in a predetermined number of clock cycles. Clock source 34 is operable for providing clock signals at a plurality of clock frequencies generally shown as clock1-clockn.

Circuits C1-Cn of integrated circuit 32 may include discrete function circuits (e.g., logic circuits for operating upon one or more inputs to implement a particular function to provide one or more outputs therefrom), such as circuits operating on one input from a sensor to provide a representative signal to further functional circuitry, transceiver circuitry, conversion circuitry, etc. Moreover, circuits C1-Cn may comprise data processing circuitry capable of performing multiple functions under program control. Alternatively, such circuits C1-Cn may implement firmware (software) functions/routines that must complete prior to some succeeding event or prior to the start of the next function. For example, as described further herein with respect to illustrative embodiments of implantable medical devices, such circuits may include digital signal processing circuits, telemetry uplink/downlink circuitry, morphology detection circuitry, arrhythmia detection circuitry, monitoring circuitry, pacing circuitry, microprocessors, and so on.

The functions performed by each of circuits C1-Cn are typically required to be completed in a particular time period prior to a next functional process being undertaken. For example, one logic circuit may perform a function in a predetermined time period to provide an output required by another circuit, or for example, a function may need to be performed by processing circuitry during a particular period of time due to the need for other processing to be performed by such processing circuitry. In another example pertaining especially to an implantable medical device, processing to complete a particular function may need to be performed in a portion of a particular time interval such as a blanking interval, an upper rate interval, an escape interval, or refractory interval of a cardiac cycle, or further, such as during a pulse generator/programmer handshake.

Clock source 34 may be configured in any manner for providing clock signals at a plurality of frequencies. Such a clock source may include any number of clock circuits wherein each provides a single clock signal at a particular frequency, clock source 34 may include one or more adjustable clock circuits for providing clock signals over a continuous range of clock frequencies, and/or clock source 34 may include a clock circuit that is operable to provide clock signals at discrete clock frequencies as opposed to over a continuous range. For example, the clock source 34 may include oscillators, clock dividers, timers, clock control circuitry or any other circuit elements required for providing clock signaling according to the present invention. Preferably, clock source 34 is configured as a continuously oscillating low frequency clock and a controllable on/off higher frequency clock.

Figure 4A:
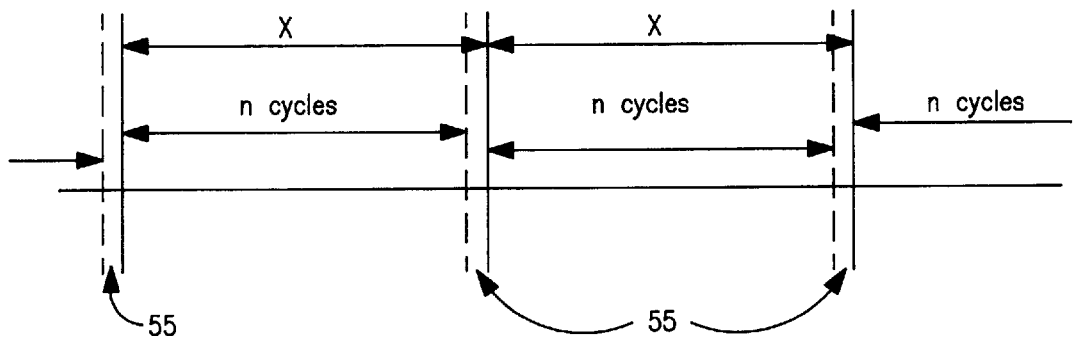
FIGS. 4A–4C show timing illustrations for use in describing the just-in-time clocking system of FIG. 3.
Figure 4B:
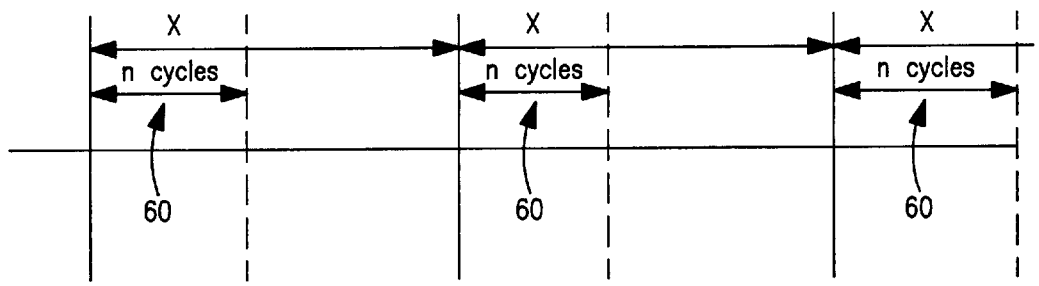
Figure 4C:
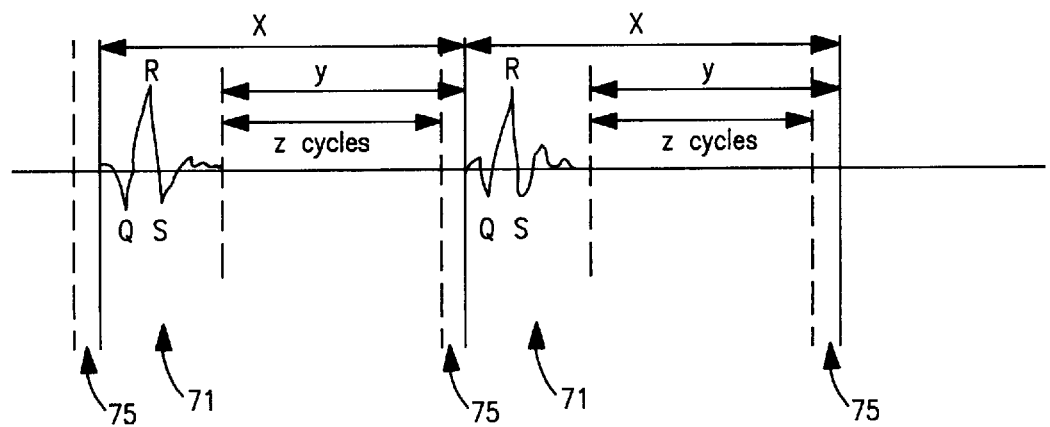

Just-in-time controllable clock operation of the just-in-time clocking system 30 of FIG. 3 is described herein in reference to FIGS. 4A–4C. As shown in FIG. 4A, time period (x) represents the time period in which a circuit, e.g., one of circuits C1-Cn, is required to complete one or more functions. The same time period (x) is shown in FIG. 4B. The time period x may be equated to any number of different time periods. For example, the time period may be the amount of time a processing circuit has to perform a particular detection function due to the need for a detection output by a certain point in time, may be a time period required to complete a particular function by a certain logic circuit so as to provide a timely output to a digital signal processing circuit, may be a time period to complete a firmware (software) routine, etc. Moreover, time period x may correspond to a cardiac cycle or a part thereof.

As shown in FIG. 4B, and according to conventional processing, circuit functions were typically performed at a burst cycle frequency and, as such, the function performed required a time period 60. Therefore, only a small amount of time (e.g., time period 60) of the entire time period x was used to perform the one or more functions requiring n cycles of time to complete. In such a case, conventionally, such burst clocks were at a substantially high clock rate, e.g., 500–1000 KHz, for such short periods of time to gain the benefit of a "duty cycle" to reduce average current drain. However, such high clock rates may not be required for carrying out such functions, or all functions.

With just-in-time clocking according to the present invention, as shown in FIG. 4A, substantially the entire time period x is used to perform the one or more functions which are completed in n cycles. In other words, the clock frequency, e.g., one of clock1-clockn, for the circuit performing the one or more functions during the time period x is set such that the one or more functions are completed in the maximum time available for performing such functions, i.e., the clock frequency is at its lowest possible value. Stated another way, a lower frequency clock is employed such that the one or more functions are performed just-in-time for other circuit or routine functionality to be performed.

In such a just-in-time manner, the clock frequency used to control the performance of such functions by the particular CMOS, CML, SOS, SOI, BICMOS, PMOS and/or NMOS circuitry is lowered resulting in reduced power consumption by such circuitry. According to calculations of dynamic power, the lower frequency results in proportional power reduction. With the lowering of the clock frequency, the integrated circuit 32 including the various circuits C1-Cn can be designed to operate at a lower frequency, e.g., as opposed to burst frequency, and also at various other frequencies depending upon need.

It is preferred that use of substantially the entire predetermined period of time result in completion of the one or more functions being performed prior to the end of the time period x as is represented by remainder time periods 55 in FIG. 4A. This remainder time period 55, for example, is preferably near or about 0 seconds.

FIG. 4C shows an illustrative timing example for processing circuitry which performs multiple functions. For example, the cardiac cycle of a patient is represented in FIG. 4C as time period x. During time period 71, i.e., during a QRS complex of the cardiac cycle, high speed processing is performed at a high clock frequency relative to a lower clock frequency used to control operation of the processing circuitry during time period y. During the time period y, when the processing circuitry is operated at a lower clock frequency, such lower clock frequency may be set such that the functions performed during z cycles are performed in substantially the entire maximum time period available for such processing, i.e., time period y. Once again, a small remainder time period 75 of the cardiac cycle time period x may exist. Such time period may be, for example, in the range of about 1.0 millisecond to about 10.0 milliseconds when the cardiac cycle is in the range of about 400 milliseconds to about 1200 milliseconds.

Figure 5:
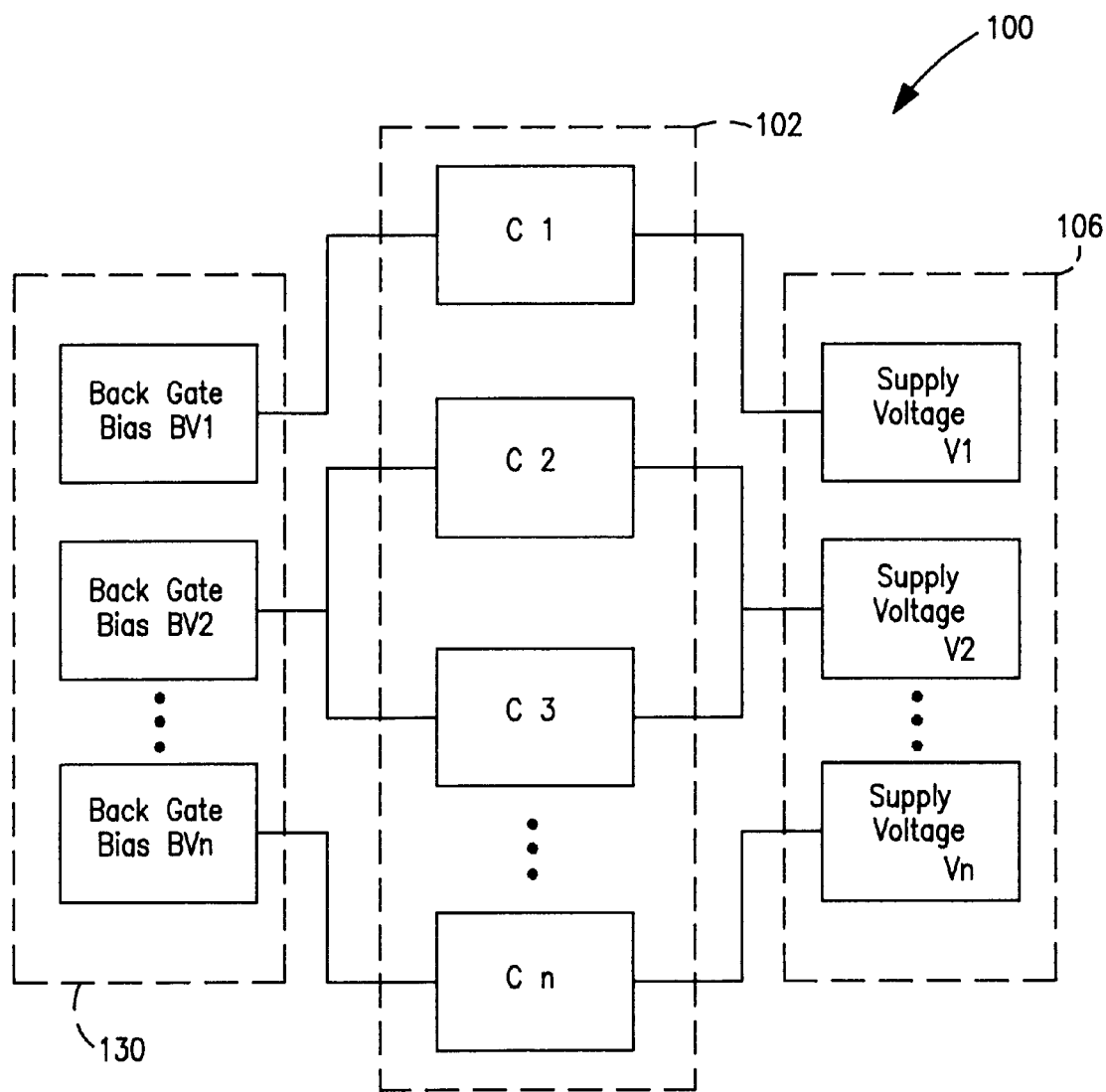
FIG. 5 is a block diagram illustration of a multiple supply voltage system according to the present invention.

FIG. 5 shows a general block diagram of a multiple supply voltage system 100 wherein one or more supply voltages are available and tailored for application to various circuits in an IC. The multiple supply voltage system 100 includes integrated circuit 102 and supply voltage source 106. Integrated circuit 102 includes circuits C1-Cn. Supply voltage source 106 is operable for providing a plurality of supply voltages V1-Vn. Each supply voltage from supply voltage source 106 is tailored to be applied to one or more circuits of circuits C1-Cn. As illustrated, supply voltage V1 is applied to circuit C1, supply voltage V2 is applied to circuit C2 and C3, and so forth.

The tailoring of the supply voltages V1-Vn to the particular circuits C1-Cn is dependent upon the frequency at which the circuits C1-Cn are required to be operated. For example, and as previously described, the logic delay of such CMOS, CML, SOS, SOI, BICMOS, PMOS and/or NMOS circuitry circuits C1-Cn increases drastically as the supply voltage is reduced to near 1 volt. If such logic delay is tolerable, the supply voltage provided to a particular circuit will drastically reduce the power consumption for that particular circuit as the energy is reduced in proportion to the square of the supply voltage ($V_{DD}$). However, if such logic delay is not tolerable, for example, if the logic circuit performs a function that must be completed within a particular period of time, the reduction of the supply voltage ($V_{DD}$) applied to such a circuit will be limited depending upon the acceptable logic delay. However, the supply voltage $V_{DD}$ for any particular circuit can be reduced as low as possible yet meet adequate speed requirements.

Integrated circuit 102 may include various different circuits C1-Cn like those described with reference to FIG. 3. The supply voltage source 106 may be implemented using a variety of components and may include any number of voltage sources wherein each provides a single supply voltage level, may include one or more adjustable voltage sources for providing supply voltage levels over a continuous range of levels, and/or may include a voltage source that is operable to provide discrete supply voltage levels as opposed to levels over a continuous range. The supply voltage source may include a voltage divider, a voltage regulator, a charge pump, or any other elements for providing the supply voltages V1-Vn. Preferably, the supply voltage source 106 is configured as a charge pump.

In the typical case, supply voltage ($V_{DD}$) is generally in the range of about 3 volts to about 6 volts. Preferably, and in accordance with the present invention, the supply voltages V1-Vn are in the range of about 1 volt to about 3 volts dependent upon the particular CMOS, CML, SOS, SOI, BICMOS, PMOS and/or NMOS technology used.

With reduction in supply voltage ($V_{DD}$), the threshold voltage ($V_T$) for the circuits is also reduced. For example, with supply voltages in the range of about 3 to about 6 volts, the threshold voltage for CMOS, CML, SOS, SOI, BICMOS, PMOS and/or NMOS devices is generally in the range of about 0.8 volts to about 1.0 volt. Preferably, in implantable medical devices, lithium chemistries are utilized for implantable batteries. Such lithium chemistries are generally in the range of about 2.8 volts to about 3.3 volts and generally the CMOS, CML, SOS, SOI, BICMOS, PMOS and/or NMOS circuitry has an associated threshold voltage of about 0.75.

By reducing the supply voltages below about 2.8 volts, voltage thresholds for CMOS, CML, SOS, SOI, BICMOS, PMOS and/or NMOS devices may be decreased to as low as about 0.2 volts to about 0.3 volts. Currently, there are various ultra low power logic designs operating at a supply voltage as low as about 1.1 volts, as for example logic circuitry for microprocessors for laptop and other portable computer applications. By utilizing the tailored supply voltages V1-Vn, low power or ultra low power logic designs may be employed for at least some of the various circuits C1-Cn of integrated circuit 102. Other circuits may require higher supply voltages. With the use of lower threshold levels due to lower supply voltages, static power consumption losses undesirably increase by several orders of magnitude.

Multiple supply voltage system 100 may therefore further optionally include back gate bias source 130 for providing back gate bias voltages BV1-BVn to circuits C1-Cn of integrated circuit 102. Generally, back gate bias voltages BV1-BVn are dependent upon the supply voltage V1-Vn applied to the circuits C1-Cn to adjust the threshold voltages for devices of circuits C1-Cn. For example, the threshold voltage ($V_T$) for the CMOS, CML, SOS, SOI, BICMOS, PMOS and/or NMOS devices of the circuit may be at a lower value by providing a back gate bias voltage to the particular circuits supplied with the lower supply voltage. Moreover, if circuit C1 is supplied with a lower supply voltage V1, then a back gate bias voltage BV1 may optionally be applied to circuit C1 to adjust the threshold voltage ($V_T$) for the CMOS, CML, SOS, SOI, BICMOS, PMOS and/or NMOS devices to a higher threshold voltage ($V_T$) value. In such a manner, static leakage current losses can be minimized because the equivalent higher threshold voltage has been restored. Moreover, a broader range of supply voltages is possible because the back gate adjustment allows a tailoring of the threshold allowing high/low speed operation and eliminating the static current drain leakage.

The back gate bias voltage may be provided by, for example, a fixed voltage source (e.g., a charge pump) connected to the back gate well via a contact. Alternatively, an active body bias scheme whereby the voltage source is selectable or adjustable over an appropriate range may be used.

Back gate voltages may be applied in manners well know in the art. The application of back gate bias voltages is described, for example, in various patent references, including U.S. Pat. No. 4,791,318 to Lewis et al., U.S. Pat. No. 4,460,835 to Masuoka, U.S. Pat. No. 5,610,083 to Chan et al. and U.S. Pat. No. 5,186,535 to Farb et al., all incorporated by reference herein in their respective entireties.

Figure 6:
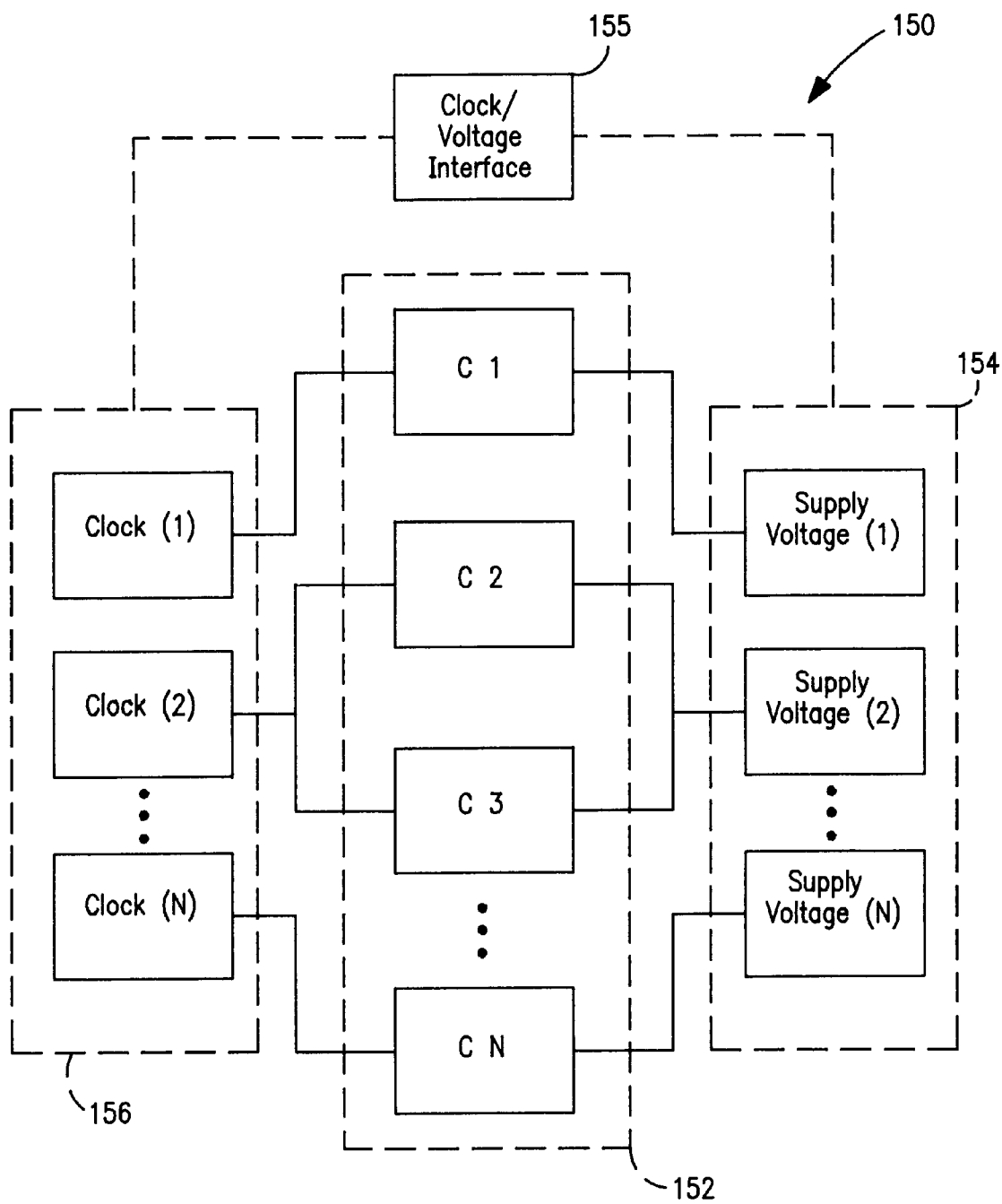
FIG. 6 is a block diagram illustrating a variable supply voltage system according to the present invention.

FIG. 6 shows a general block diagram of a variable supply voltage/variable clock system 150 according to the present invention. System 150 includes integrated circuit 152, clock source 156, supply voltage source lo 154, and clock/supply voltage interface 155. Supply voltage source 154 is operable for providing a plurality of supply voltages V1-Vn to a plurality of circuits C1-Cn of integrated circuit 152. Clock source 156 of system 150 is operable for providing clock signals at a plurality of frequencies, clock1-clockn. Circuits C1-Cn are of a similar nature to those described with reference to FIG. 3. Clock source 156 is similar to the clock source 34 as described with reference to FIG. 3. Supply voltage source 154 is similar to supply voltage source 106 described in reference to FIG. 5. In variable supply voltage/variable clock system 150, however, clock/voltage interface 155 is employed to adjust supply voltages V1-Vn applied to the circuits C1-Cn "on the fly," as required by specific timing functions required by or inherent to circuits C1-Cn.

As an illustrative example, circuit C1 may be a particular logic circuit for performing one or more particular functions. Such functions may be required to be performed, however, in a first time period at a first clock frequency and during a different second time period at a second clock frequency so that such function may be performed within the allowed time of the respective first and second time periods. That is, one time period is shorter than the other and, as such, the functions which require performance over a certain number of cycles must be performed at a higher clock frequency if it is to be completed within a time period that is shorter than another time period.

In such an example, and according to the present invention, clock/voltage interface 155 detects the clock signal applied to circuit C1 during the first time period in which the higher frequency clock signal is used and accordingly provides supply voltage source 154 with a signal to select and apply a certain supply voltage corresponding to the higher clock frequency. Thereafter, when the lower clock frequency is applied to circuit C1 during the second time period, clock/voltage interface 155 senses the use of the lower clock frequency and applies a signal to voltage supply source 154 for application of a certain supply voltage corresponding to the lower clock frequency for application to circuit C1.

Figure 7:
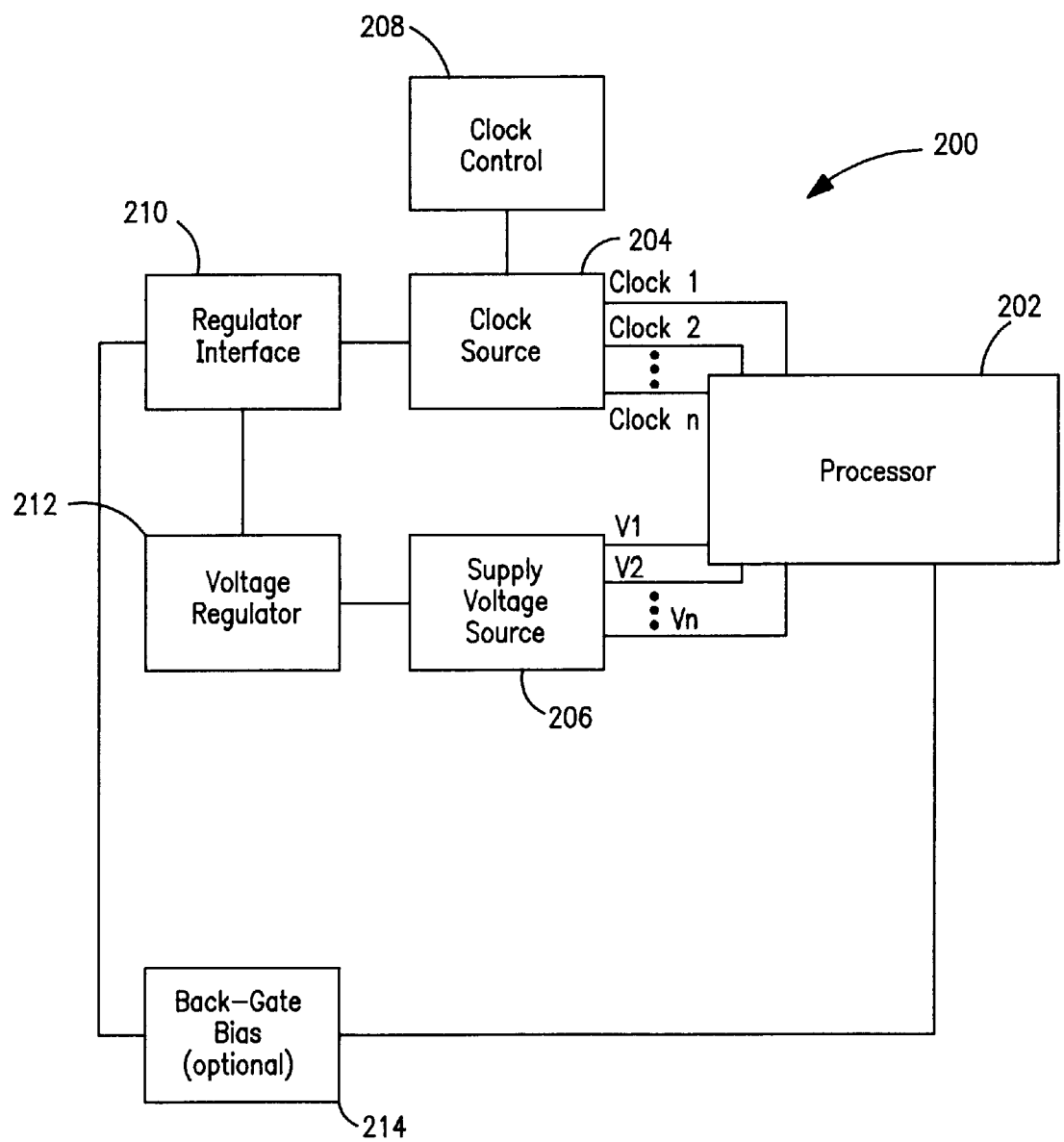
FIG. 7 is a block diagram of clock controlled processing circuitry according to the present invention.

In another example, circuit C2 may be a CMOS, CML, SOS, SOI, BICMOS, PMOS and/or NMOS processor which may also have clock frequency and corresponding supply voltage adjustments made "on the fly." Such a system will become readily apparent to those skilled in the art from the following discussion referring to FIG. 7.

FIG. 7 shows a general block diagram of clock controlled processing system 200 according to the present invention. Clock controlled processing system 200 includes processor 202 (e.g., a CMOS, CML, SOS, SOI, BICMOS, PMOS and/or NMOS microprocessor or CMOS, CML, SOS, SOI, BICMOS, PMOS and/or NMOS digital signal processor), clock source 204, supply voltage source 206, voltage regulator 212, regulator interface 210, clock control 208, and optional back gate bias source 214. In a manner similar to that described in reference to FIG. 6, the supply voltage 206 applied to processor 202 is changed "on the fly," as required by specific circuit timing requirements.

Generally, processor 202 is operated under control of clock source 204. Depending upon the processing capability required, clock source 204 may operate processor 202 at any one of a plurality of clock frequencies. Such clock frequencies may be selected under the control of clock control 208. Clock control 208 may be part of any timing and control hardware and/or timing and control software used to control operation of processor 202 as part of a larger system. Such clock control may take the form, for example, of a digital controller/timer circuit for performing timing control of an implantable medical device.

Processor 202 may perform any number of functions as appropriate for the device in which it is used. High frequency processing capabilities (i.e., about 250 KHz to about 10 MHz), low frequency processing capabilities (i.e., about 1 Hz to about 32 KHz), and processing capabilities with regard to frequencies between such limits are contemplated according to the present invention. For simplicity purposes, clock control processing system 200 operation shall be described with reference to processor 202 performing only two different functions, each during a predetermined respective period of time. For example, with respect to an implantable medical device such as a pacemaker, during the first period of time, a high processing function requiring a relatively high clock frequency may include a function such as telemetry uplink/downlink, morphology detection, initialization, arrhythmia detection, far-field R-wave detection, EMI detection, retrograde conduction, etc. On the other hand, low frequency processing functions may include a function such as sensing intrinsic beats, pacing, low speed telemetry, transtelephonic data transfer, remote monitoring, battery checks, etc.

When processor 202 performs high frequency processing functions during a predetermined time period, a relatively high clock frequency (e.g., about 250 KHz to about 10 MHz) may be supplied by clock source 204 for operation of processor 202. Regulator interface 210 will detect the higher clock frequency applied to processor 202 for operation during the high processing function and apply a control signal to voltage regulator 212 for regulation of the supply voltage source 206. Supply voltage source 206 is operable under control of voltage regulator 212 to provide a supply voltage within a predetermined range, preferably between about 1.1 volts and about 3 volts. When a high clock frequency is employed to operate processor 202 for high frequency processing functions, supply voltage source 206 generally applies a supply voltage in the upper range of the preferred supply voltages to the CMOS, CML, SOS, SOI, BICMOS, PMOS and/or NMOS devices of processor 202.

On the other hand, when processor 202 executes low frequency processing functions during predetermined periods of time, clock control 208 signals clock source 204 to apply a lower frequency for operation of processor 202. As such, regulator interface 210 detects the lower frequency being used to operate processor 202 and issues a control signal to voltage regulator 212 for regulation of supply voltage source 206 such that a lower supply voltage in the lower end of the preferred range of supply voltages is applied to the CMOS, CML, SOS, SOI, BICMOS, PMOS and/or NMOS devices of processor 202.

It will be recognized by those skilled in the art that any intermediate processing capability may be achieved between the higher frequency and the lower frequency capabilities described hereinabove, and that the scope of the present invention is not limited to processing at only two clock frequencies and at two corresponding supply voltages. Instead, multiple levels of processing capability may be achieved according to the present invention with associated clock frequencies and corresponding supply voltages being applied to processor 202.

FIG. 4C illustrates one embodiment of the clock control processing system 200 of the present invention. As shown in FIG. 4C, during the overall cardiac cycle of predetermined time period x, a high frequency is employed to control operation of processor 202 during time period 71 of the cardiac cycle time period x (e.g., during processing of the QRS complex). Thereafter, a lower clock frequency is used during time period y for controlling operation of processor 202 to perform any of a number of other different functions, such as cardiac event/EMI differentiation functions. During operation of the processor 202 at the higher clock frequency during time period 71, a higher supply voltage from supply voltage source 206 is applied to the CMOS, CML, SOS, SOI, BICMOS, PMOS and/or NMOS circuitry devices of processor 202. Likewise, during operation of the processor 202 at the relatively lower clock frequency, a lower supply voltage from supply voltage source 206 is applied to the CMOS, CML, SOS, SOI, BICMOS, PMOS and/or NMOS devices of processor 202 during time period y of the overall cardiac cycle time period x.

Moreover, and as shown in FIG. 7, an optional back gate bias 214 may be used to dynamically adjust the threshold voltage ($V_T$) of CMOS, CML, SOS, SOI, BICMOS, PMOS and/or NMOS circuitry devices of processor 202 as a function of the clock frequency applied to processor 202 by clock source 204. The regulator interface 210 detects the clock frequency used to control operation of processor 202 and controls the voltage level of back gate bias 214 to be applied to the CMOS, CML, SOS, SOI, BICMOS, PMOS and/or NMOS devices of processor 202. The dynamic adjustment of the threshold voltage may be implemented as an adjustable or selectable voltage source utilizing, for example, a charge pump and a regulator. The back gate voltage and the "normal" gate voltage provide a gate bias or voltage to the transistor. By adjusting the back gate voltage, the "apparent" voltage is increased with a resultant reduction in leakage current.

Figure 8:
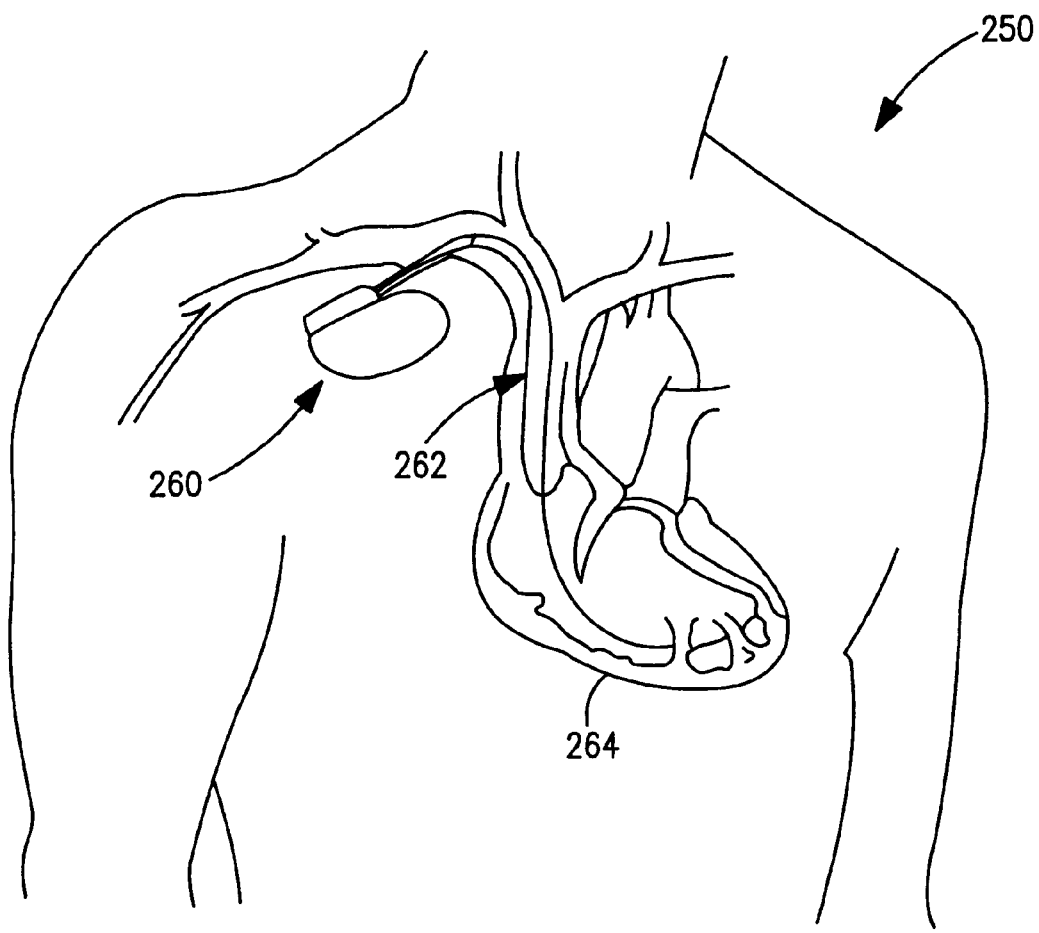
FIG. 8 is a diagram illustrating an implantable medical device in a body.

FIG. 8 is a simplified diagram of implantable medical device 260 for which the present invention finds particularly efficacious application. Implantable medical device 260 is implanted in body 250 near human heart 264. Implantable medical device 260 is connected to heart 264 by leads 262. In the case where device 260 is a pacemaker, leads 262 may be pacing and sensing leads for sensing electrical signals attendant to the depolarization and repolarization of heart 264, and for providing pacing pulses in the vicinity of the distal ends thereof.

Implantable medical device 260 may be any implantable cardiac pacemaker such as those disclosed in U.S. Pat. No. 5,158,078 to Bennett et al., U.S. Pat. No. 5,387,228 to Shelton, U.S. Pat. No. 5,312,453 to Shelton et al., or U.S. Pat. No. 5,144,949 to Olson, all hereby incorporated herein by reference in their respective entireties and which can all be modified according to the present invention.

Figure 10:
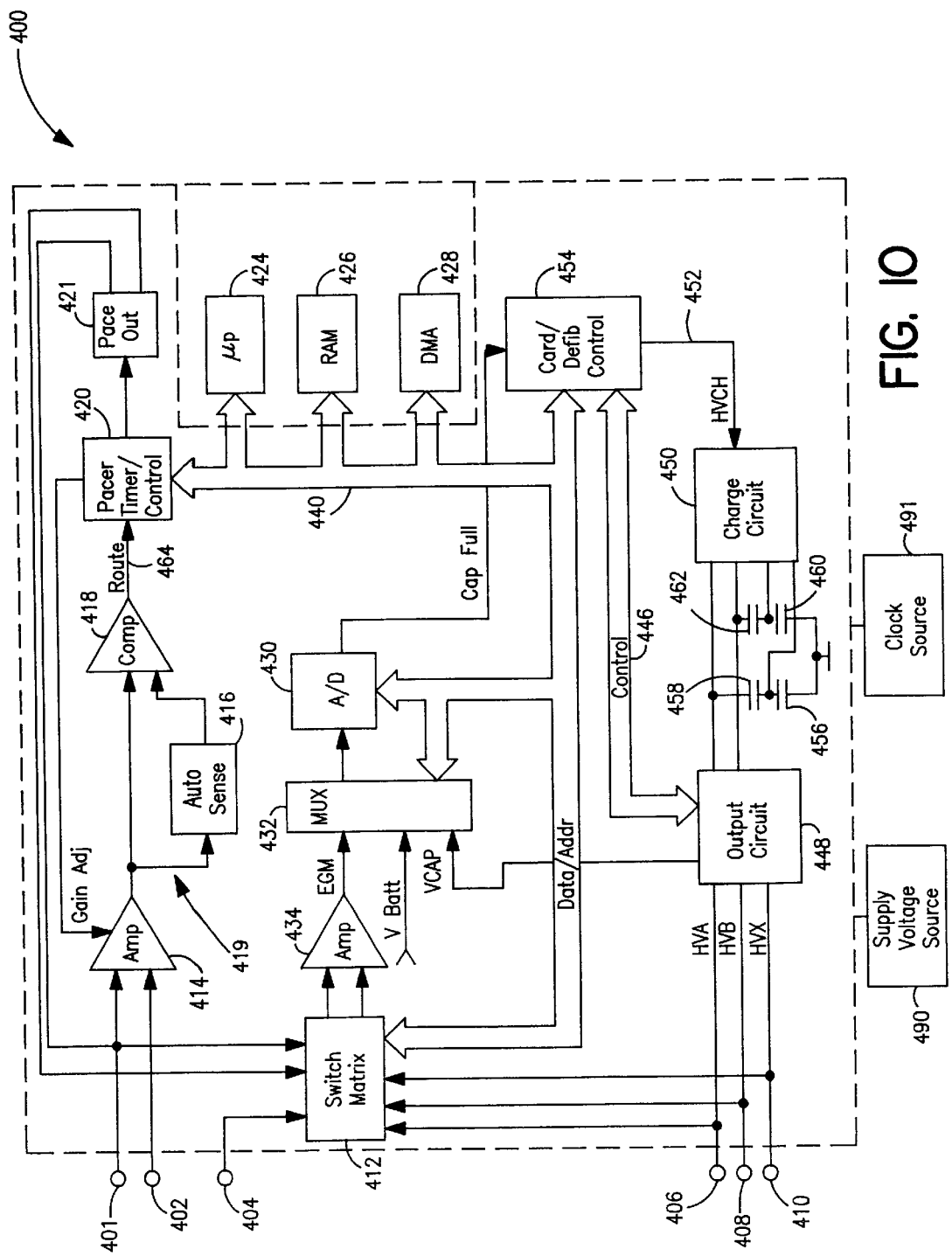
FIG. 10 is a schematic block diagram of an implantable pacemaker/cardioverter/defibrillator (PCD) for illustrating one or more embodiments of the present invention.

Implantable medical device 260 may also be a pacemaker/cardioverter/defibrillator (PCD) corresponding to any of the various commercially-available implantable PCDs, one of which is summarily described herein with reference to FIG. 10 and described in detail in U.S. Pat. No. 5,447,519. In addition to the PCD described in U.S. Pat. No. 5,447,519, the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties. Those devices may be employed using the present invention in that such devices may employ or be modified with circuitry and/or systems according to the present invention.

Alternatively, implantable medical device 260 may be an implantable nerve stimulator or muscle stimulator such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties.

Finally, implantable medical device 260 may be a cardioverter, an implantable pulse generator (IPG) or an implantable cardioverter-defibrillator (ICD).

It is to be understood, however, that the scope of the present invention is not limited to implantable medical devices or medical devices only, but includes any type of electrical device which employs CMOS, CML (Current Mode Logic), SOS (Silicon on Sapphire), SOI (Silicon on Insulator), BICMOS, PMOS and/or NMOS circuitry or circuit design where low power consumption is desired.

In general, implantable medical device 260 includes an hermetically-sealed enclosure that includes an electrochemical cell such as a lithium battery, CMOS circuitry that controls device operations, and a telemetry transceiver antenna and circuit that receives downlinked telemetry commands from and transmits stored data in a telemetry uplink to an external programmer. The circuitry may be implemented in discrete logic and/or may include a microcomputer-based system with A/D conversion.

It is to be understood that the present invention is not limited in scope to particular electronic features and operations of particular implantable medical devices and that the present invention may be useful in conjunction with various implantable devices. Moreover, the present invention is not limited in scope to implantable medical devices including only a single processor but may be applicable to multiple-processor devices as well.

Figure 9:
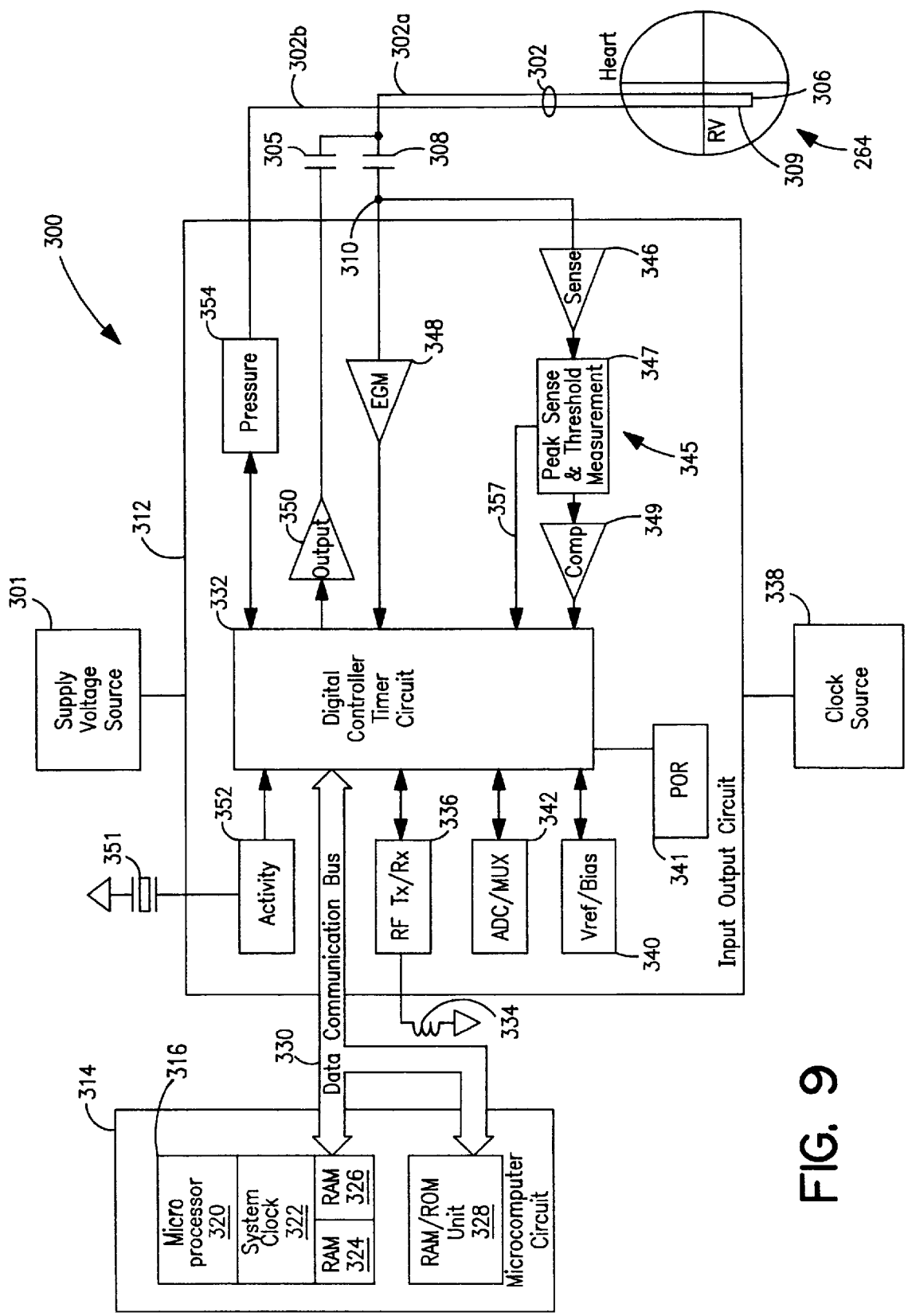
FIG. 9 is a block diagram of the circuitry of a pacemaker for use in illustrating one or more embodiments of the present invention.

FIG. 9 shows a block diagram illustrating the components of pacemaker 300 in accordance with one embodiment of the present invention. Pacemaker 300 has a microprocessor-based architecture. Illustrative pacemaker 300 of FIG. 9 is only one exemplary embodiment of such devices, however, and it will be understood that the present invention may be implemented in any logic-based, custom integrated circuit architecture or in any microprocessor-based system.

In the illustrative embodiment shown in FIG. 9, pacemaker 300 is most preferably programmable by means of an external programming unit (not shown in the figures). One such programmer suitable for the purposes of the present invention is the commercially available Medtronic Model 9790 programmer. The programmer is a microprocessor-based device which provides a series of encoded signals pacemaker 300 by means of a programming head which transmits radio frequency (RF) encoded signals to antenna 334 pacemaker 300 according to a telemetry system such as, for example, that described in U.S. Pat. No. 5,127,404 to Wyborny et al., the disclosure of which is hereby incorporated by reference herein in its entirety. It is to be understood, however, that any programming methodology may be employed so long as the desired information is transmitted to and from the pacemaker.

Pacemaker device 300 illustratively shown in FIG. 9 is electrically coupled to the patient's heart 264 by leads 302. Lead 302a including electrode is 306 is coupled to a node 310 in the circuitry pacemaker 300 through input capacitor 308. Lead 302b is coupled to pressure circuitry 354 of input/output circuit 312 to provide a pressure signal from sensor 309 to the circuit 354. The pressure signal is used to ascertain metabolic requirements and/or cardiac output of a patient. Further, activity sensor 351, such as a piezoceramic accelerometer, provides a sensor output to activity circuit 352 of input/output circuit 312. The sensor output varies as a function of a measured parameter that relates to metabolic requirements of a patient. Input/output circuit 312 contains circuits for interfacing to heart 264, to activity sensor 351, to antenna 334, to pressure sensor 309 and circuits for application of stimulating pulses to heart 264 to control its rate as a function thereof under control of software-implemented algorithms in microcomputer unit 314.

Microcomputer unit 314 preferably comprises on-board circuit 316 that includes microprocessor 320, system clock circuit 322, and on-board random access memory (RAM) 324 and read only memory (ROM) 326. In this illustrative embodiment, off-board circuit 328 comprises a RAM/ROM unit. On-board circuit 316 and off-board circuit 328 are each coupled by a communication bus 330 to digital controller/timer circuit 332.

According to the present invention, the circuits shown in FIG. 9 are powered by an appropriate implantable battery supply voltage source 301 (e.g., a voltage source generally shown in FIGS. 1–7). For the sake of clarity, the coupling of supply voltage source 301 to various circuits pacemaker 300 is not shown in the figures. Further, the circuits operable under control of a clock signal shown in FIG. 9 are operated according to the present invention under clock source 338. For the sake of clarity, the coupling of such clock signals from the clock source 338 (e.g., a clock source generally shown in FIGS. 1–7) to such CMOS, CML, SOS, SOI, BICMOS, PMOS and/or NMOS circuits of pacemaker 300 is not shown in the Figures.

Antenna 334 is connected to input/output circuit 312 to permit uplink/downlink telemetry through RF transmitter and receiver unit 336. Unit 336 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

$V_{REF}$ and bias circuit 340 generates a stable voltage reference and bias currents for circuits of input/output circuit 312. Analog-to-digital converter (ADC) and multiplexer unit 342 digitize analog signals and voltages to provide "real-time" telemetry intracardiac signals and battery end-of-life (EOL) replacement function. A power on reset circuit 341 functions as a means to reset circuitry.

Operating commands for controlling the timing pacemaker 300 are coupled by bus 330 to digital controller/timer circuit 332, where digital timers and counters establish the overall escape interval of pacemaker 300 as well as various refractory, blanking, and other timing windows for controlling the operation of the peripheral components disposed within input/output circuit 312.

Digital controller/timer circuit 332 is preferably coupled to sense circuitry 345 and to electrogram (EGM) amplifier 348 for receiving amplified and processed signals sensed by electrode 306 disposed on lead 302a. Such signals are representative of the electrical activity of the patient's heart 264. Sense amplifier 346 of circuitry 345 amplifies sensed electrocardiac signals and provides an amplified signal to peak sense and threshold measurement circuitry 347. Circuit 347 in turn provides an indication of peak sensed voltages and measured sense amplifier threshold voltages on path 357 to digital controller/timer circuit 332. An amplified sense amplifier signal is also provided to comparator/threshold detector 349. The sense amplifier may correspond to that disclosed in U.S. Pat. No. 4,379,459 to Stein, which is hereby incorporated by reference herein in its entirety.

The electrogram signal provided by EGM amplifier 348 is employed when the implanted device 300 is being interrogated by an external programmer (not shown) to transmit by uplink telemetry a representation of an analog electrogram of the patients electrical heart activity. Such functionality is, for example, shown in U.S. Pat. No. 4,556,063 to Thompson et al., previously incorporated by reference.

Output pulse generator and amplifier 350 provides pacing stimuli to the patient's heart 264 through coupling capacitor 305 and electrode 306 in response to a pacing trigger signal provided by digital controller/timer circuit 332. Output amplifier 350 may correspond generally to the output amplifier disclosed in U.S. Pat. No. 4,476,868 to Thompson, also incorporated by reference herein in its entirety. The circuits of FIG. 9 comprise CMOS, CML, SOS, SOI, BICMOS, PMOS and/or NMOS circuitry capable of operation according to the present invention include processor 320, digital controller timer circuit 332, RAM 324, ROM 326, RAM/ROM unit 328 and ADC/Mux 342.

FIG. 10 is a functional schematic diagram from U.S. Pat. No. 5,447,519 to Peterson, which shows implantable PCD 400 in which the present invention may usefully be practiced. This diagram is an illustration to be taken only as an exemplary type of device in which the invention may be embodied, and not as limiting to the scope of the present invention. Other implantable medical devices as previously described having functional organizations wherein the present invention may be useful may also be modified in accordance with the present invention. The present invention is also believed to be useful, for example, in conjunction with implantable PCDs such as those disclosed in U.S. Pat. No. 4,548,209 to Wielders et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their respective entireties.

Illustrative PCD 400 is provided with six electrodes 401, 402, 404, 406, 408, and 410. Electrodes 401 and 402 may be a pair of closely-spaced electrodes, for example, that are positioned in the ventricle of heart 264. Electrode 404 may correspond to a remote, indifferent electrode located on the housing of the implantable PCD 400. Electrodes 406, 408, and 410 may correspond to large surface area defibrillation electrodes located on leads to the heart 264 or epicardial electrodes.

Electrodes 401 and 402 are shown as hard-wired to the near field (i.e., narrowly spaced electrodes) R-wave detector circuit 419 comprising band pass filtered amplifier 414, auto threshold circuit 416 (for providing an adjustable sensing threshold as a function of the measured R-wave amplitude), and comparator 418. An Rout signal 464 is generated whenever the signal sensed between electrodes 401 and 402 exceeds a sensing threshold defined by auto threshold circuit 416. Further, the gain on amplifier 414 is adjusted by pacer timer and control circuitry 420. The sense signal, for example, is used to set the timing windows and to align successive waveshape data for morphology detection purposes. For example, the sense event signal 464 may be routed through the pacer/timer control circuit 420 on bus 440 to processor 424 and may act as an interrupt for the processor 424 such that a particular routine of operations, e.g., morphology detection, discrimination functions, is commenced by processor 424.

Switch matrix 412 is used to select available electrodes under control of processor 424 via data/address bus 440 such that the selection includes two electrodes employed as a far field electrode pair (i.e., widely spaced electrodes) in conjunction with a tachycardia/fibrillation discrimination function (e.g., a function to discriminate between tachycardia, i.e., an abnormally fast heart rate, and fibrillation, i.e., uncoordinated and irregular heartbeats, so as to apply an appropriate therapy). Far field EGM signals from the selected electrodes are passed through band pass amplifier 434 and into multiplexer 432, where they are converted to digital data signals by analog to digital converter (ADC) 430 for storage in random access memory 426 under control of direct memory access circuitry 428. For example, a series of EGM complexes for several seconds may be performed.

According to the present invention, the circuits shown in FIG. 10 are powered by an appropriate implantable battery supply voltage source 490 (e.g., a voltage source generally shown in FIGS. 1–7). For the sake of clarity, the coupling of supply voltage source 490 to various circuits of the PCD 400 is not shown in the figures. Further, the circuits operable under control of a clock signal shown in FIG. 10 are operated according to the present invention under clock source 491. For the sake of clarity, the coupling of such clock signals from the clock source 491 (e.g., a clock source generally shown in FIGS. 1–7) to such CMOS, CML, SOS, SOI, BICMOS, PMOS and/or NMOS circuits of PCD 400 is not shown in the figures.

The occurrence of an R-wave sense event or detect signal Rout 464 is communicated to processor 424 to initiate morphology analysis on waveforms by processor 424 for use in selection of a therapy for heart 264. For example, the processor may calculate the cumulative beat-to-beat variability of heart 264, time intervals separating R-wave sense events, and various other functions as set out in numerous references including any of the references already listed herein and various other references with regard to implantable PCDs.

Other portions of the PCD 400 of FIG. 10 are dedicated to the provision of cardiac pacing, cardioversion, and defibrillation therapies. With regard to cardiac pacing, the pacer timing/control circuit 420 includes programmable digital counters which control the basic timing intervals associated with cardiac pacing, including the pacing escape intervals, the refractory periods during which sensed R-waves are ineffective to restart timing of escape intervals, etc. The durations of such intervals are typically determined by processor 424 and communicated to pacer timer/control circuit 420 via address/data bus 440. Further, under control of processor 424, pacer timing/control circuit also determines the amplitude of such cardiac pacing pulses and pace out circuit 421 provides such pulses to the heart.

In the event that a tachyarrhythmia (i.e., tachycardia) is detected, and an anti-tachyarrhythmia pacing therapy is desired, appropriate timing intervals for controlling generation of anti-tachycardia pacing therapies are loaded from processor 424 into pacer timing and control circuitry 420. Similarly, in the event that generation of a cardioversion or defibrillation pulse is required, processor 424 employs the counters and timing and control circuitry 420 to control timing of such cardioversion and defibrillation pulses.

In response to detection of fibrillation or a tachycardia requiring a cardioversion pulse, processor 424 activates cardioversion/defibrillation control circuitry 454, which initiates charging of the high voltage capacitors 456, 458, 460 and 462 via charging circuit 450 under control of high voltage charging line 452. Thereafter, delivery of the timing of the defibrillation or cardioversion pulse is controlled by pacer timing/control circuitry 420. Various embodiments of an appropriate system for delivering and synchronization of cardioversion and defibrillation pulses, and controlling the timing functions related to them is disclosed in more detail in U.S. Pat. No. 5,188,105 to Keimel, which is incorporated herein by reference in its entirety. Other such circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,375,817 to Engle et al., all incorporated herein by reference in their entireties. Further, known circuitry for controlling the timing and generation of anti-tachycardia pacing pulses is described in U.S. Pat. No. 4,577,633 to Berkovits et al., U.S. Pat. No. 4,880,005 to Pless et al., U.S.

Pat. No. 4,726,380 to Vollmann et al., and U.S. Pat. No. 4,587,970 to Holley et al., all of which are incorporated herein by reference in their entireties.

Selection of a particular electrode configuration for delivery of the cardioversion or defibrillation pulses is controlled via output circuit 448 under control of cardioversion/defibrillation control circuit 454 via control bus 446. Output circuit 448 determines which of the high voltage electrodes 406, 408 and 410 will be employed in delivering the defibrillation or cardioversion pulse regimen.

The components of PCD 400 of FIG. 10 comprise CMOS, CML, SOS, SOI, BICMOS, PMOS and/or NMOS circuitry capable of operation according to the present invention include processor 424, control circuits 420 and 454, RAM 426, DMA 428, ADC 430, and multiplexer 432.

According to the present invention, pacemaker 300 illustrated in FIG. 9 and PCD 400 illustrated in FIG. 10 may both be implemented in accordance with the generalized embodiments previously described herein with reference to FIGS. 1–7. First, for example, with respect to pacemaker 300 of FIG. 9, voltage supply source 301 of pacemaker 300 may be implemented in a manner previously described with reference to FIGS. 1–7. Likewise, clock source 338 of pacemaker 300 may be implemented in such a manner as described with reference to FIGS. 1–7. Clock source 491 of PCD 400 of FIG. 10 and the voltage supply source 490 of PCD 400 of FIG. 10 may be implemented in accordance with the generalized embodiments previously described herein with reference to FIGS. 1–7.

As one illustrative example, ADC/Mux 342, RF transmitter/receiver 336, digital controller timer circuit 332, and various other CMOS, CML, SOS, SOI, BICMOS, PMOS and/or NMOS circuits may be individually operated at different clock frequencies available from clock source 338. Likewise, such circuits may be operated at corresponding supply voltages which may be different for each of the circuits. Moreover, RF transmitter/receiver 336 may be operated during a particular time period (e.g., when uplinking) at a particular clock frequency available from clock source 338 and at a particular supply voltage available from voltage supply source 301 corresponding to the particular clock frequency. On the other hand, during a different time period (e.g., during downlink), circuit 336 may be operated at a completely different clock frequency and supply voltage. Automatic adjustment of telemetry parameters under certain circumstances is described in U.S. Pat. No. 5,683,432 to Goedeke et al., hereby incorporated by reference herein in its entirety.

In respect of FIG. 10, A/D converter circuit 430, cardioverter/defibrillator control circuit 454, and various other circuits such as RAM 426, DMA 428, and multiplexer 432 may also be operated at different clock frequencies available from clock source 491 and at different corresponding supply voltages available from supply voltage source 490. A telemetry circuit (not shown in the Figures) may be employed with PCD 400 of FIG. 10 and may also be operated at different clock frequencies available from clock source 491 and at different corresponding supply voltages available from supply voltage source 490. Additionally, processor 424 may be operated at different clock speeds, depending upon the function being performed by processor 424 (such as described with reference to FIG. 7). Morphology detection sensing at typical physiologic rates (i.e., 50 to 150 BPM), for example, may be performed at a first clock frequency and corresponding supply voltage while arrhythmia detection may be performed at a different clock frequency and corresponding supply voltage.

Figure 11:
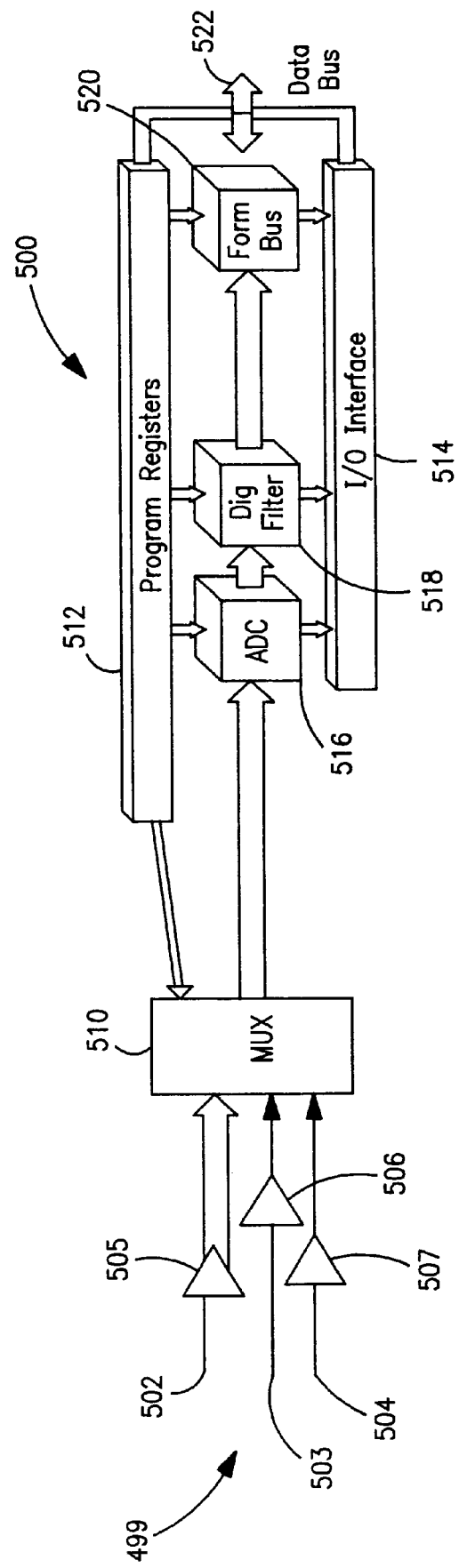
FIG. 11 is a schematic block diagram illustrating a variable clock/variable supply voltage digital signal processing system according to the present invention.

FIG. 11 shows variable clock/variable supply voltage digital signal processing (DSP) system 500 which may be employed in conjunction with and/or in the alternative to certain circuits shown in FIGS. 9 and 10. DSP system 500 according to FIG. 11, for example, may be employed in place of activity circuit 352, pressure circuit 354, sense amplifier circuit 346 (for P-wave, R-wave- and/or T-wave sense amplifiers), and further may be provided with additional functionality with use of pseudo EKG signal 502. Generally, any number of analog signals 499, for example, such as pseudo EKG signals 502, activity sensor signal 503 and pressure and onset sensor signal 504, are provided through respective amplifiers 505–507. The amplified signals are presented to multiplexer 510 which provides them to analog to digital converter (ADC) 516 of the digital signal processing system 500 in a cycled fashion.

Signals 502–504 may be cycled at different rates by cycling through the outputs of the several amplifiers/preamplifiers 505–507 such as described in pending U.S. patent application Ser. No. 081801,335, Medtronic Docket No. P-4521, entitled "Method for Compressing Digitized Cardiac Signals Combining Lossless Compression and Non-linear Sampling," which describes variable compression via ADC sampling and which is incorporated herein by reference in its entirety. The ADC may also have variable conversion rates as described in U.S. Pat. No. 5,263,486 and U.S. Pat. No. 5,312,446, incorporated by reference herein in their respective entireties.

Input/output interface 514 and program registers 512 are utilized under control of a timing circuit (not shown) to control application of the analog signals from multiplexer 510 to ADC 516 of the DSP system 500 which provides such converted digital signals to digital filter 518 to provide a waveform for analysis to waveform analysis processor 520 (i.e., a digital signal processor (DSP)) of system 500. To reduce power, the waveform analysis (DSP) processor 520 is clocked at different speeds, i.e., controlled "on the fly," according to the present invention, depending upon the processing needs.

Only during a QRS complex, for example, does waveform analysis processor 520 operate in a high speed processing mode at a relatively high frequency. During the remainder of the cardiac cycle the DSP processor 520 may be "idling along" at a much lower clock frequency. Such a processing cycle has been previously described with reference to FIG. 4C. In addition to the lower clock speed utilized for different portions of the cardiac cycle, one skilled in the art will recognize that in accordance with the other aspects of the present invention, as the speed is reduced, the supply voltage level ($V_{DD}$) may also be reduced accordingly. Thus, the objective of reduced power consumption is realized.

Figure 12:
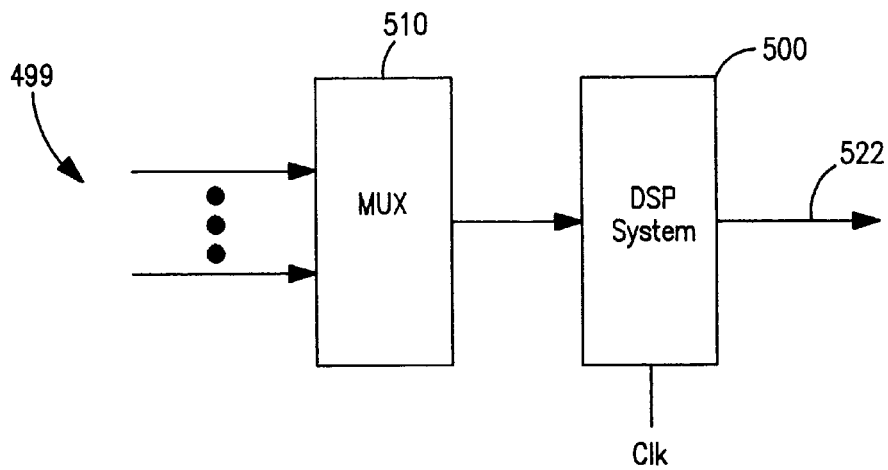
FIG. 12 is a schematic block diagram generally illustrating the system of FIG. 11.

DSP system 500 of FIG. 11 is generally shown in FIG. 12. Generally, DSP systems, such as DSP system 500, may include an input filter, an ADC, a sample and hold circuit (sometimes built into the ADC), and a digital signal processor to provide an output. The input filter, ADC, and sample and hold circuit provide data representative of an analog input to the processor. The digital signal processor can then be used to implement one of various algorithms, such as, for example, digital filtering, mapping the input, performing morphology detection, functioning as sense amplifiers (P-wave, R-wave, or T-wave), etc., to provide a desired output.

As used in a medical device described herein, the output of DSP system 500 is generally provided to a controller in digital form. Such a digital output resulting from digital processing may, however, be converted back into an analog output using components common to DSP systems such as a digital to analog (DAC) converter, output filters, etc. One skilled in the art will recognize that depending upon the application of the present invention, the components of DSP system 500 may vary. For example, one DSP system may include a DAC to provide an analog output, while another such system may not.

As shown in FIG. 12, two or more analog input signals 499 are multiplexed by multiplexer 510 and converted to digital data representative thereof for processing by the digital signal processor of DSP system 500. The data representative of the input signals is then operated upon by the digital signal processor of DSP system 500 to perform functions with regard thereto during a predetermined period of time. R-wave detection algorithms and P-wave detection algorithms may be performed, for example, by the same digital signal processor during the predetermined time period using data representative of ventricular and atrial analog input signals, respectively, provided to the multiplexer 510.

Such multiplexing of the input signals and use of a single digital signal processor as shown in FIGS. 11 and 12 to perform multiple functions in a predetermined period of time requires the digital signal processor of the DSP system 500 to be operated at a relatively high clock frequency. The clock frequency is relatively high compared to the clock frequencies that would be required if multiple digital signal processors were used to perform the functions in the same time period. With operation at a relatively high frequency to accomplish the multiple functions during this predetermined period of time, a relatively high supply voltage must also be applied to the processor for operation.

The supply voltage is relatively high compared to the supply voltage that would be required if multiple digital signal processors were used to perform the functions in the same time period. As such, the dynamic power (P) consumed by the single digital signal processor ($(P)=\frac{1}{2}CV_{DD}^2F$, where C is nodal capacitance, F is the clock or switching frequency, and $V_{DD}$ is the supply voltage for the processor) is rather high. The formula for calculating dynamic power (P) indicates that dynamic power consumption of CMOS, CML, SOS, SOI, BICMOS, PMOS and/or NMOS circuits is proportional to the square of the supply voltage ($V_{DD}$). In addition, the dynamic power (P) is proportional to the switching or clock frequency (F). As described below, the same multiple functions as performed above using a single DSP system can be accomplished using multiple DSP systems operating at lower clock frequencies and lower supply voltages to reduce power consumption.

Figure 13:
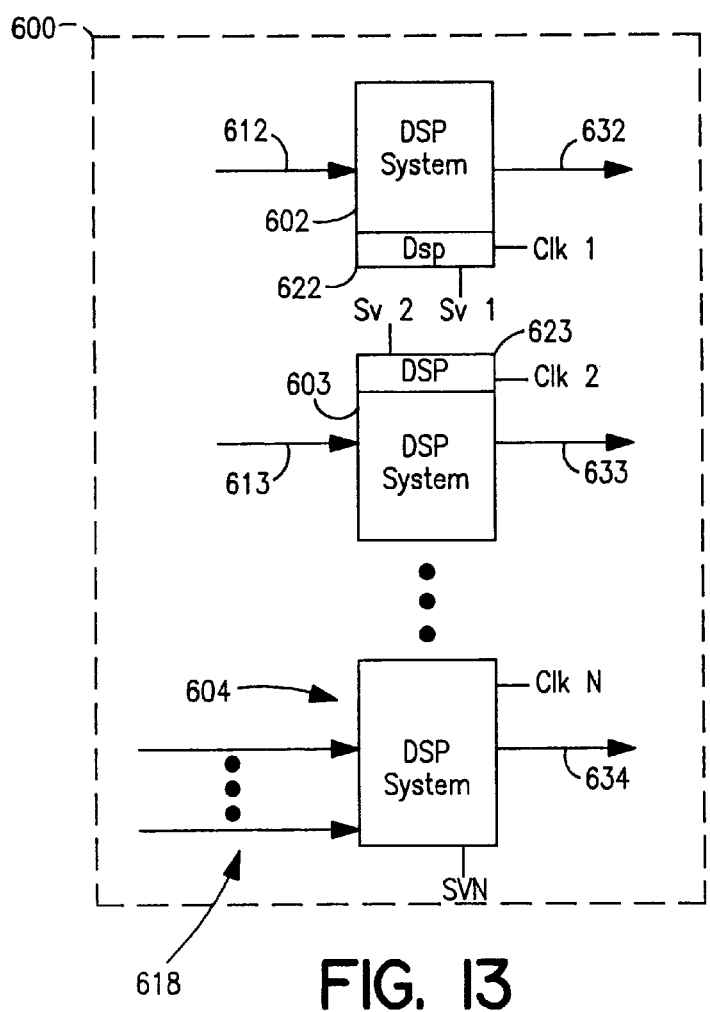
FIG. 13 is a schematic block diagram generally illustrating reduction in power consumption using multiple digital signal processing systems according to the present invention.

FIG. 13 shows a generalized schematic illustration of such a multiple processor system 600 including multiple DSP systems 602–604 for reducing power consumption according to the present invention. DSP system 602 is provided with a first analog input signal 612 and includes conversion circuitry for converting the analog input signal 612 to digital data representative thereof. Digital signal processor 622 of the DSP system 602 then operates on the data to perform a function and provide an output 632 (which may be converted back to an analog signal if desired). The digital signal processor 622 is operated at a first clock frequency Clk1 and a first supply voltage SV1 is applied to the digital signal processor 622.

DSP system 603 is provided with a second analog input signal 613 and includes conversion circuitry for converting the analog input signal 613 to digital data representative thereof. Digital signal processor 623 of the DSP system 603 then operates on the data to perform a function and provide an output 633 (which may be converted back to an analog signal if desired). The digital signal processor 623 is operated at a second clock frequency Clk2 and a second supply voltage SV2 is applied to the digital signal processor 623.

Generally, the first and second clock frequencies Clk1 and Clk2 at which the first and second digital signal processors operate to perform their respective functions in a predetermined time period, are lower relative to the clock frequency necessary for a single processor to perform the same functions in the same predetermined time period. The first and second clock frequencies Clk1 and Clk2 are such that the power consumed by the first and second digital signal processors in performance of the respective functions during the predetermined period of time is less than the power that would be consumed if only one of the first and second digital signal processors were to perform both the respective functions within the predetermined time period.

Likewise, supply voltages SV1 and SV2 may also be reduced because the digital signal processors 622 and 623 are running at a lower speed and a decrease in clock frequency allows use of lower supply voltages as previously described herein. If the clock frequency Clk1 is reduced, for example, SV1 applied to the digital signal processor 622 may also be reduced.

By way of example, consider the case in which system 600 includes only DSP system 602 and DSP system 603. Each of DSP systems 602 and 603 receives a single analog input 612 and 613, respectively. Digital signal processor 622 operates on the data representative of analog input 612 at clock frequency Clk1 to perform a first function. Digital signal processor 623 operates on the data representative of the analog input 613 at clock frequency Clk2 to perform a second function. In comparison to the power consumed by a system such as that shown in FIG. 12 (where a single processor is used to perform both the functions within the predetermined period of time using multiplexed inputs), multiple digital signal processors may perform the same functions, but while consuming substantially less power.

More particularly, by using two digital signal processors in accordance with the present invention, the dynamic power so consumed (P2) may be computed by the formula:

$$(P2)=\tfrac{1}{2}(2C)((V_{DD}/2)^2(F/2)$$

where C is two times the nodal capacitance because there are two digital signal processors, F/2 is the reduced clock or switching frequency because both the digital signal processors can operate at ½ the speed as compared to a single processor attempting to complete both functions in the predetermined period of time, and $V_{DD}/2$ is the supply voltage because the digital signal processors are running at ½ speed as compared to the single processor attempting to complete both functions in the predetermined time period.

Power consumed by the two digital signal processors illustration is given by the formula:

$$P2=\tfrac{1}{2}C(V_{DD}^2/4)F$$

which is ¼ the power consumed by the single processor using multiplexed inputs as described above in respect of FIG. 12. One skilled in the art will now recognize that the foregoing two digital signal processor embodiment of the present invention occupies more integrated circuit die area than a single processor having multiplexed inputs. Power consumption is greatly reduced, however.

In the illustrative embodiment described above, the clock frequencies at which the first and second digital signal processors operate are substantially equal. Those clock frequencies need not be the same or substantially the same, however, to reduce power consumption, and indeed may be different. The first and second clock frequencies Clk1 and Clk2 at which the first and second digital signal processors operate to perform the respective functions are most preferably frequencies selected such that the power consumed by the first and second digital signal processors in performance of the respective functions during the predetermined period of time is less than the power that would be consumed if only one of the first and second digital signal processors were to perform both of the functions within the predetermined time period.

Moreover, and as shown in FIG. 13, more than two DSP systems, such as additional DSP system 604, may be employed to reduce power consumption. Additionally, each of the digital signal processors, including DSP systems 602–604, may be provided with one or more analog inputs as represented generally by inputs 618 which may be multiplexed as described with respect to FIG. 11, or alternatively may be provided with a single input as shown above with respect to DSP systems 602 and 603.

Use of multiple DSP systems is particularly beneficial when processing higher frequency analog signals, although such systems may be employed with any analog signal. Such multiple DSP configurations find particularly advantageous application, for example, when employed for P-wave, R-wave, and T-wave sensing, EMI detection, sensor signal processing of such signals as pressure, oxygen saturation, blood flow and cardiac contractility signals, telemetry functions, and the like. Such functions may be characterized generally by the bandwidth of the analog signals being processed to perform such functions. In general, the bandwidth of analog signals such as cardiac sense signals is in the range of between about 10 Hz and about 100 Hz (as opposed to some sensor signals, such as pressure signals, having a bandwidth of between about 1 Hz and about 10 Hz).

Figure 14:
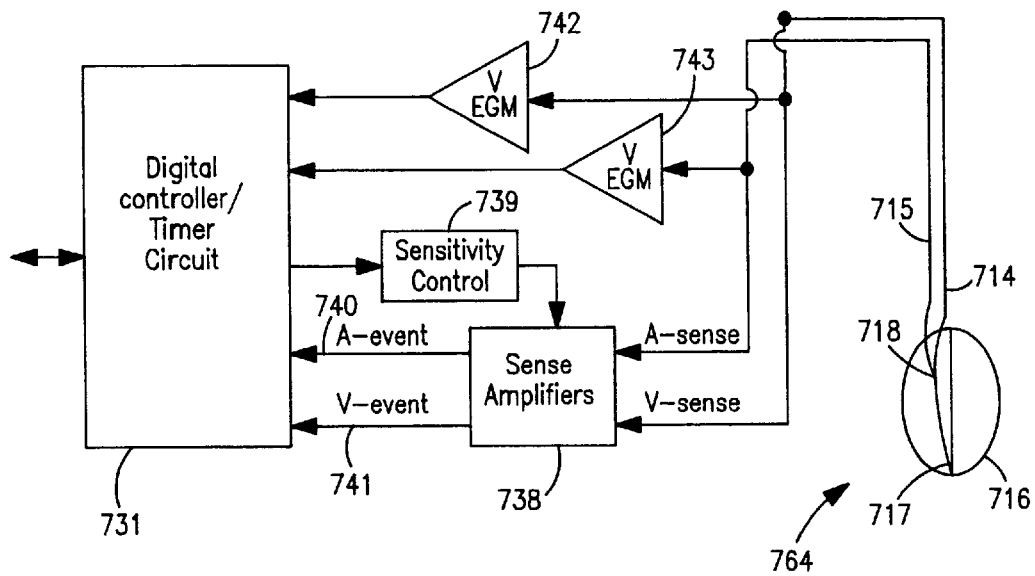
FIG. 14 is a schematic block diagram of a portion of cardiac pacemaker including sense amplifiers for receiving cardiac sense signals.
Figure 15:
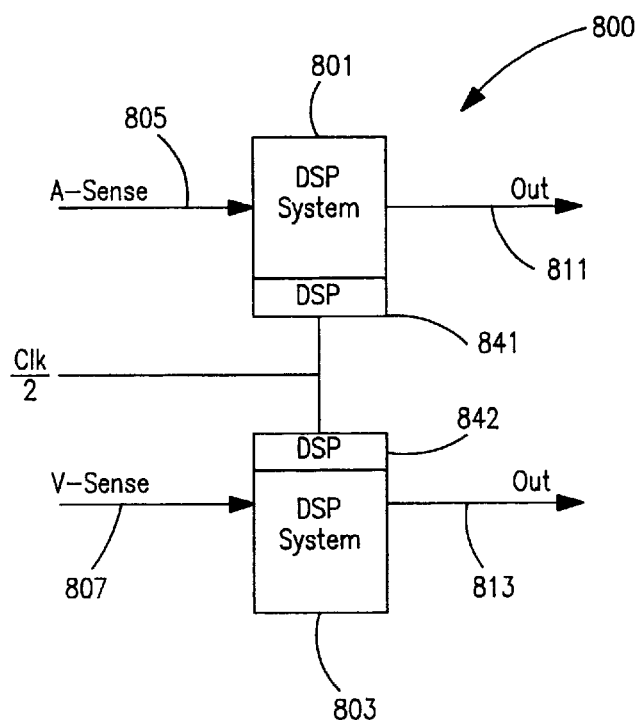
FIG. 15 is a two digital signal processing system embodiment of a system according to FIG. 13 illustrating implementation of the sense amplifier functions illustrated in FIG. 14 according to the present invention.

FIGS. 14 and 15 illustrate the use of multiple DSP systems to perform multiple functions required for operation of a cardiac pacemaker. FIG. 14 shows some components conventionally used in a cardiac pacemaker such as that described in U.S. Pat. No. 5,387,228 to Shelton, entitled "Cardiac Pacemaker With Programmable Output Pulse Amplitude and Method," issued Feb. 7, 1995. For simplicity, other components of the pacemaker, such as those previously described herein and which are also described in other documents referenced herein such as in U.S. Pat. No. 5,387,228, are not described in further detail.

Referring again to FIG. 14, digital controller/timer circuit 731 is coupled to sensing circuitry including sense amplifier circuit 738 and a sensitivity control circuit 739. More particularly, digital controller/timer circuit 731 receives an A-event (atrial event) signal on line 740, and a V-event (ventricular event) signal on line 741. Sense amplifier circuit 738 is coupled to leads 714 and 715 and receives V-Sense (ventricular sense) and A-Sense (atrial sense) signals from heart 764. Sense amplifier circuit 738 asserts the A-event signal on line 40 when an atrial event (i.e., a paced or intrinsic atrial event) is detected, and asserts the V-event signal on line 741 when a ventricular event (paced or intrinsic) is detected. Sense amplifier circuit 738 includes one or more sense amplifiers corresponding, for example, to that disclosed in U.S. Pat. No. 4,379,459 to Stein. Sensitivity control circuit 739 is provided to adjust the gain of sense amplifier circuit 738 in accordance with programmed sensitivity settings, as will be appreciated by those skilled in art of pacing.

Ventricular electrocardiogram amplifier 742 is coupled to a conductor in lead 714 to receive a V-sense signal from heart 764. Similarly, atrial electrocardiogram amplifier 743 is coupled to one conductor of lead 715 to receive the A-sense signal from heart 764. The electrocardiogram signals developed by amplifiers 742 and 743 are used on those occasions when the implanted device is being interrogated by an external programmer for uplink telemetry.

FIG. 15 shows an embodiment of multiple DSP system 800 in accordance with the present invention for replacing sensing circuitry 738 shown in FIG. 14. Multiple DSP system 800 includes two DSP systems 801 and 803. DSP system 801 includes a digital signal processor 841 which operates on data representative of the A-sense signal 805 originating from the atrium of the heart. Further, DSP system 803 includes a digital signal processor 842 which operates on data representative of the V-sense signal 807 originating from the ventricle of the heart. By way of example of the present invention, digital signal processor 841 detects when an atrial event (P-wave detection) occurs using the data representative of the A-sense signal during a predetermined period of time. In another example of the present invention, digital signal processor 843 detects when an ventricular event (R-wave detection) occurs using the data representative of the V-sense signal during the predetermined period of time.

As shown in FIG. 15, the digital signal processors operate at clock frequencies that are ½ of the clock frequency necessary for operation of a single digital signal processor (assuming the corresponding single digital signal processor receives, via a multiplexer, both A-sense and V-sense signals and performs both the atrial and ventricular detection functions during the predetermined period of time). As such, and as described above in the general two digital signal processor illustration, the power so consumed is substantially reduced using the two digital signal processors for performing the respective functions within the predetermined period of time in respect of the power that would otherwise be required for a single processor to perform the same functions during the same time period.

Additionally, and as described above, the supply voltage may also be reduced because the digital signal processors are running at ½ speed and a decrease in clock frequency permits use of lower supply voltages. Power consumption is reduced because power the consumed is directly proportional to the square of the supply voltage. If the clock frequency of the digital signal processors is reduced in half, for example, relative to a single processor embodiment using multiplexed inputs, the supply voltage may also be reduced in half relative in respect of the supply voltage employed in a single processor embodiment.

Upon detecting an atrial event, DSP system 801 provides an A-event signal at output 811. Upon detecting a ventricular event, DSP system 803 provides a V-event signal at output 813. The sense amplifier functions illustrated in FIG. 14 are therefore accomplished using the two DSP system embodiment of the present invention shown in FIG. 15, with a corresponding reduction in power consumption in respect of the use of a single DSP system to accomplish the same functions (such as those illustrated in FIG. 12).

Those skilled in the art will recognize that other signals may be processed according to the present invention with the same or additional digital signal processors, controllers, microprocessors and/or systems. For example, such DSP systems may be used for T-wave detection, oxygen sensor data analysis, pressure sensor data analysis, cardiac contractility data analysis, EMI detection, or for processing and analyzing any other signals or data sets may benefit from the use of digital signal processing.

The present invention is compatible with various fabrication technologies such as silicon on insulator (SOI), silicon on sapphire (SOS), current mode logic (CML), BICMOS, PMOS and NMOS CMOS technologies, as well as to conventional silicon CMOS technologies. The present invention as described herein is enabling technology in respect of the employment of multiple DSP systems to perform more functions and computations due to the manner in which power consumption may be reduced for such multiple DSP systems. Moreover, multiple processor based designs may also be implemented in accordance with the present invention due to reduced power consumption resulting from supply voltages and clocking frequencies being reduced for various functions and computations performed by the processors.

Additionally, as power consumption is reduced, further functionality may be added to devices in accordance with the present invention to provide a device having added functionality yet lower or the same power consumption relative to conventional prior art devices. A processor in accordance with the present invention may perform, for example, various morphology detection functions such as differentiation of retrograde P-waves and antegrade P-waves of EGM waveform; differentiation of P-waves from far field R-waves; differentiation of AF-A flutter-AT from sinus tachycardia; differentiation of VT-VF-V flutter from SVT; differentiation of cardiac signals from electromagnetic interference; etc. Also by way of example, various embodiments of the present invention may also be employed to detect or filter out electromagnetic interference (EMI) emanating from or generated by theft detectors, conductive signals, RF noise, myopotentials, and the like.

Figure 16:
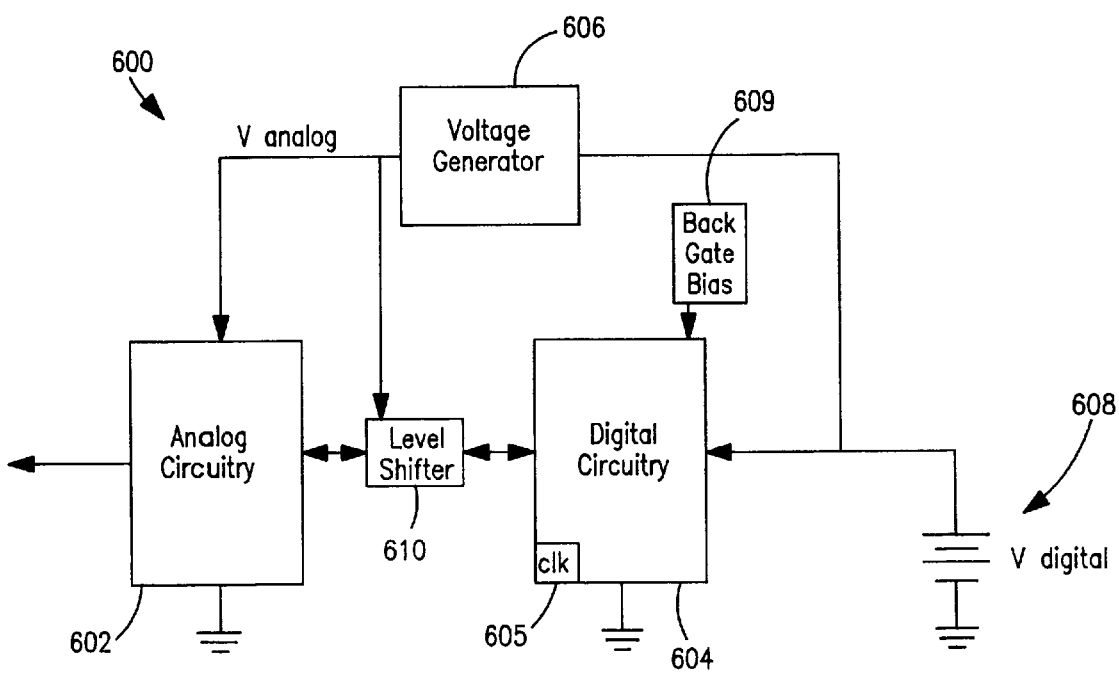
FIG. 16 is a general schematic block diagram of a device according to the present invention using different supply voltages for analog and digital circuits of the device.

FIG. 16 is a general schematic block diagram of device 600 including analog circuitry 602 and digital circuitry 604 (including clock circuit 605). The digital circuitry (e.g., CMOS, CML, SOS, SO, BICMOS, PMOS and/or NMOS technology) has a fixed supply voltage ($V_{digital}$) applied thereto from power source 608, which may be any type of electrochemical cell or battery suitable for use in an implantable medical device and providing an appropriate supply voltage. Some examples of batteries or cells finding application in respect of the present invention include, but are not limited to, lithium iodine, lithium manganese, nickel cadmium, nickel metal hydride, zinc manganese oxide, zinc silver oxide, zinc mercuric oxide, lithium silver vanadium oxide, lithium ion, divalent silver oxide and silver oxide electrochemical cells and batteries. At least some of the foregoing chemical systems may require stepping down of voltage for use in certain embodiments of the present invention.

Fixed supply voltage $V_{digital}$ applied for operation of the digital circuitry is kept low to reduce power consumption as previously described herein. Power consumed by the CMOS, CML, SOS, SOI, BICMOS, PMOS and/or NMOS circuitry, for example, is proportional to the square of the supply voltage. Therefore, a lower supply voltage is necessary to reduce power consumption.

Particularly for implantable devices, however, designing analog circuitry 602 to function at such low supply voltages is difficult due to various considerations, such as small circuit headroom, small signal amplitudes (which may effectively reduce amplifier sensitivity), small signal-to-noise ratios, reduced common mode rejection ratios (CMRR), reduced transmitted telemetry power, voltage regulation and current source problems, and so on.

As such, in accordance with the present invention, device 600 further most preferably includes voltage generator circuit 606 to generate at least one fixed supply voltage ($V_{analog}$) for application to analog circuitry 602. Voltage generator circuit 606 is supplied with supply voltage $V_{digital}$ to generate supply $V_{analog}$. Voltage generator circuit 606 may generate any number of predetermined or fixed voltages greater than $V_{digital}$ to supply different analog circuits. For example, output circuits may require a larger voltage than other amplification circuits. Voltage generator circuit 606 will generate both +/− supplies ($V_{DD}$ and $V_{SS}$) to power only the analog circuitry 602.

Digital circuitry 604 is supplied with the lower voltage $V_{digital}$. For example, as contemplated in the present invention, lower fixed or predetermined supply voltage $V_{dgital}$ is in the range of about 1.1 to 1.5 volts at beginning-of-life (BOL) and about 0.8 volts to about 1.0 volts at end-of-life (EOL). The generated fixed supply voltage $V_{analog}$ is in the range of about +/− 2.0 volts to about +/− 3.0 volts.

Level shifter 610 may be used to translate logic and/or control signals between the analog circuitry 602 and the digital circuitry 604. Such level shifting may be required due to the difference in supply voltage being applied to the respective digital circuitry 604 and analog circuitry 602.

As described previously above, with reduction in supply voltage ($V_{DD}$), threshold voltage ($V_T$) for the circuits is also reduced. With use of lower threshold levels due to lower supply voltages, static power consumption losses undesirably increase by several orders of magnitude. A back gate bias source 609 may therefore be used to provide back gate bias voltages to digital circuitry 604. In this manner, static leakage current losses can be minimized because the equivalent higher threshold voltage has been restored. The back gate bias voltage may be provided by, for example, a fixed voltage source (e.g., a charge pump) connected to the back gate well via a contact. Alternatively, an active body bias scheme whereby the voltage source is selectable or adjustable over an appropriate range may be used. Back gate voltages may be applied in any known manner, such as those previously described herein.

Figure 17:
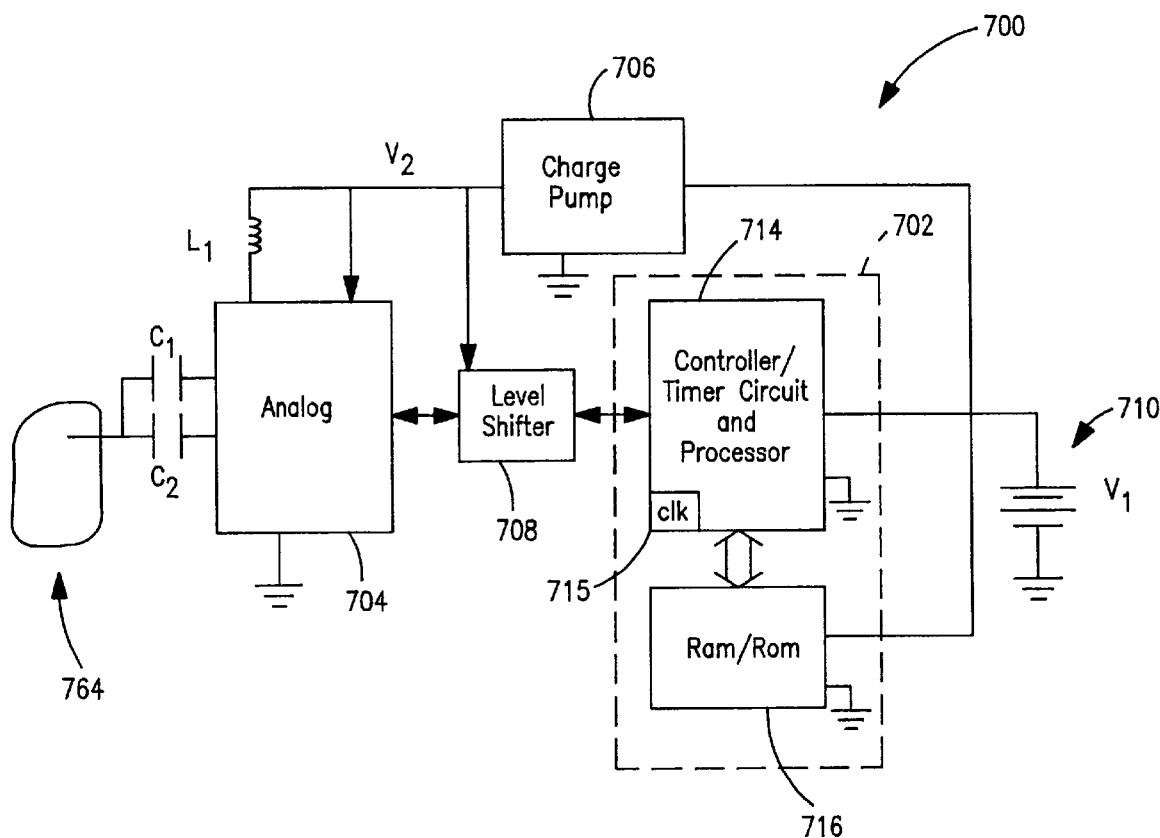
FIG. 17 is a more detailed schematic block diagram of one embodiment of a pacemaker much like that shown in FIG. 9 according to the present invention wherein a lower supply voltage is applied to the digital circuits of the pacemaker with a charge pump being used to generate a higher supply voltage to be applied to the analog circuits of the pacemaker.

FIG. 17 is a more detailed schematic block diagram of one embodiment of pacemaker 700 much like that shown in FIG. 9. According to the present invention, a lower supply voltage V1 (e.g., 1.1 volt source 710) is applied to digital circuitry 702 of pacemaker 700 with charge pump circuit 706 being used to generate at least one higher supply voltage V2 (e.g., 3.0 volts) to be applied to analog circuitry 704 of pacemaker 700.

Digital circuitry 702 may, for example, include circuits such as those described above in reference to pacemaker 300 and FIG. 17. Digital circuitry 702 may include, for example, controller/timer and processor circuit 714 (including a clock circuit 715) or memory circuits such as RAM/ROM circuits 716 for communication with controller/timer and processor circuit 714. Such components and functionality are described herein with reference to FIG. 9.

Analog circuitry 704 may include the analog circuits of pacemaker 300 described previously in reference to FIG. 9. Such analog circuits may include, for example, atrial and ventricular sense amplifiers for receiving A-sense signals from the atrium of heart 764 and for receiving V-sense signals from the ventricle of heart 764. Such sense amplifier circuits are coupled to leads extending to heart 764 via capacitors C1 and C2 to receive the V-Sense (ventricular sense) and A-Sense (atrial sense) signals from heart 764. Sense amplifier circuits then communicate an A-event signal to controller 714 when an atrial event (i.e., an intrinsic atrial event or P-wave) is detected, and communicate a V-event signal to controller 714 when a ventricular event (an intrinsic R-wave) is detected. Analog circuitry 704 may also include bandpass filters and detection circuitry to accomplish such detection. Moreover, analog circuitry 704 may include circuitry for T-wave detection, such as a T-wave amplifier, bandpass filter, or capture detection circuitry.

Analog circuitry 704 may include various other circuits, such as analog to digital converters (ADCs); voltage reference and current source circuits; telemetry transmission and reception circuitry; sensor amplification circuitry, and bandpass, detection, and drive circuitry to be used with such sensors (e.g., minute ventilation activity, pressure, temperature, pH, pCO2 or oxygen sensors); ECG amplifiers and bandpass filters, such as amplifiers for A-sense signals, V-sense signals and T-wave signals to be used for telemetry purposes; output circuits and pump circuits such as those described in U.S. Pat. No. 5,387,228 to Shelton; battery monitor circuits; power on reset circuits; and any circuits generally designed as analog circuits.

Figure 18:
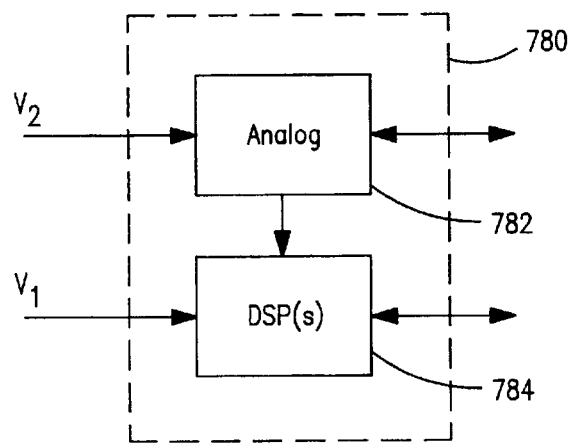
FIG. 18 is a block diagram illustrating the use of digital signal processor(s) in the embodiment shown in FIG. 17.

FIG. 18 shows an alternative embodiment for at least some of the analog circuitry 704 described in reference to FIG. 17. The functions of some of the analog circuits, for example sense amplifiers, may be implemented using circuitry 780 which includes analog circuits 782 (e.g., preamplifiers, ADC's, etc.) and further includes one or more digital signal processors (DSP's) 784 to perform analysis with respect to data communicated thereto by way of analog circuits 782. A similar illustrative implementation is described hereinabove in respect of FIG. 11. As such, and according to the present invention as described in reference to FIGS. 16 through 18, supply voltage V1 is applied to DSP(s) 784 while charge pumped voltage V2 is used as the supply voltage for analog circuits 782.

Charge pump circuit 706 is used to generate both +/− voltage supplies (VDD and VSS) to power analog circuitry 704. Various configurations for charge pump circuit 706 may be used. Charge pump circuit 706 may be implemented, for example, using the techniques described in U.S. Pat. No. 5,387,228 to Shelton. Charge pump circuit 706 may, for example, be regulated, such as with use of a charge comparator circuit to regulate the voltage, or charge pump circuit 706 may be unregulated. The unregulated voltage may vary as the voltage source V1 varies due to low battery conditions, for example. Yet further, one or more supply voltages may be output from charge pump circuit 706 as voltage V1 is pumped to different amplitudes. More than one supply voltage may be provided by charge pump circuit 706 or more than one charge pump circuit 706 may be employed to provide multiple supply voltages, where each charge pumped voltage is greater than supply voltage V1. That is, one charge pumped voltage may exceed another charged pumped voltage.

Supply voltages V1 and V2 described in reference to FIG. 17 (i.e., wherein different supply voltages are applied to analog circuitry and digital circuitry, respectively) are fixed predetermined voltages. In other words, pumped predetermined fixed voltage V2 is applied to the analog circuits whenever they are in operation, as opposed to a pumped voltage being applied to circuits only when low battery conditions are apparent. Such voltages are determined at the time the circuits are designed and do not vary other than possibly when batteries have even lower states of charge.

Additionally, pacemaker 700 may include level shifter 708. Level shifter 708 may be used to translate logic and/or control signals between analog circuitry 704 and controller and processor 714. Such level shifting may be required due to the difference in supply voltages being applied to digital circuitry 702 and analog circuitry 704, respectively. Such a voltage level shifter may be implemented in various configurations. For example, illustrative voltage level shifters are described in U.S. Pat. No. 4,663,701, hereby incorporated by reference herein in its entirety.

Embodiments of the clock speed control and voltage supplies of the present invention other than those shown in FIGS. 9, 10 and 11 are now described. The embodiments of the present invention described hereinabove generally rely upon circuit design and/or firmware control to adjust device power consumption and timing parameters. Such adjustments are typically based on a present logic status or situation sensed in the circuitry of the device, or are triggered or controlled by a firmware program such as upon initiation or completion of a subroutine. A potential limitation of such embodiments is the amount of time required to effect a change in clock frequency or to increase or decrease voltage supply levels.

In another embodiment of the present invention that will now be described, key parameters or signals, or characteristics thereof such as amplitude, frequency and/or phase, are measured, sensed or detected before they are routed into or between Digital Controller Timer Circuit 332 and/or Microcomputer Circuit 314, thereby permitting earlier prediction and/or enablement of power reduction and/or power increase. In such an embodiment of the present invention, circuit and firmware power needs are predicted on the basis of expected usage by monitoring data or signal inputs, data or signal outputs and/or signal statistics using a control algorithm (more about which we say below) to control and direct functional parameters relating to the efficient delivery and control of electrical power.

Figure 19:
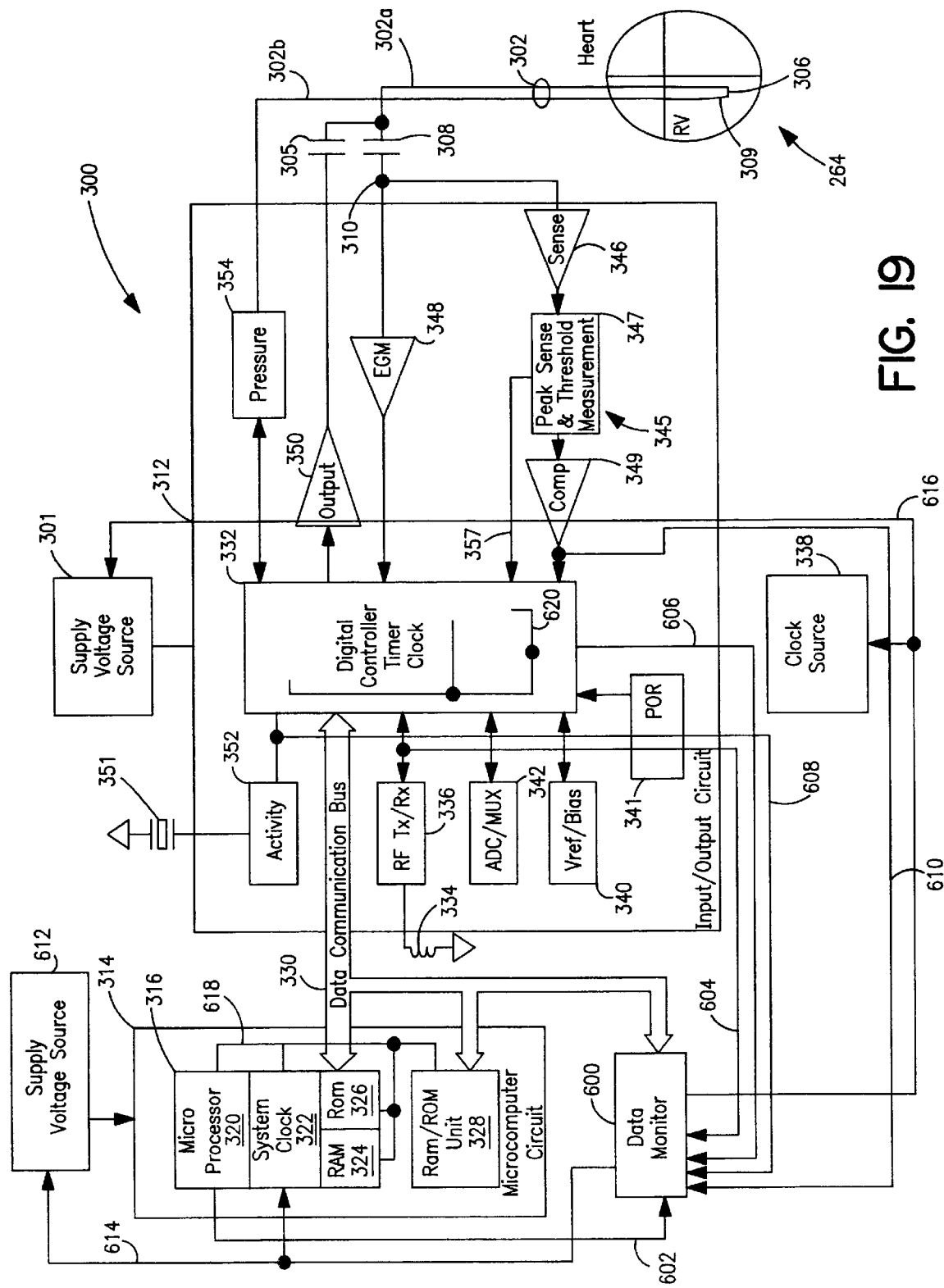
FIG. 19 shows a block diagram of one embodiment of the present invention.

FIG. 19 shows one such embodiment of the present invention where, for example, any one or more of an output of comparator 349 (which is also an input to Digital Controller Timer Circuit 332), an output of clock source 338, an output of supply voltage source 301, an output of Activity Sensor 352, and/or an output of RF Tx/Rx 336 are monitored by Data Monitor 600.

Other signals, inputs or outputs may also be monitored by Data Monitor 600 of the present invention, including, but not limited to, the following examples:

(1) Type and/or frequency of sensed events. Examples include, but are not limited to, sensed normal intrinsic sensed events, premature atrial contractions (PACs), premature ventricular contractions (PVC's), atrial and/or ventricular tachycardia, atrial and/or ventricular flutter, atrial and/or ventricular fibrillation, noise, electromagnetic interference, muscle signals, far-field R-waves (FFRW), antegrade or retrograde p-waves, and the like;

(2) Type and/or frequency of downlink or uplink telemetry transmissions. Examples include, but are not limited to, sensed complete memory data dumps, sensed selected memory location uplinks, detected re-transmissions in a noisy environment such as those described in U.S. Pat. No. 5,292,343 to Blanchette et al., sensed telemetry distance, transmission power, receiver sensitivity, bit error rate (BER), the amount of data telemetered or received such as described in U.S. Pat. No. 5,683,432 to Goedeke et al., and the like;

(3) Type and/or frequency of sensed signals. Examples include, but are not limited to, high sensed sampling rates such as the sensed activity rate response signals described in U.S. Pat. No. 4,428,378 to Anderson et al. or the sensed cardiac acceleration signals described in U.S. Pat. No. 5,496,351 to Plicchi et al., low sensed sampling rates second such as those described in U.S. Pat. No. 5,562,711 to Yerich et al., and sensed oxygen saturation signals such as those described in U.S. Pat. No. 4,791,935 to Baudino et al.;

(4) Intra-circuit block activity per unit time (i.e. transition activity). Examples include, but are not limited to, sensing activity in individual circuit blocks of Digital Controller Timer Circuit 332 (not shown in FIG. 19);

(5) Firmware sub-program activity per unit time. Examples include, but are not limited to, sensing the number and/or type of operand codes processed per unit time by microprocessor 320 using a program stored in RAM 324, ROM 326, or RAM/ROM unit 328. For example, divide or multiply operand codes typically require more clock cycles to execute than do add or shift operand codes;

(6) Data streams. Examples include, but are not limited to, sensed telemetry data formatting and movement, sensed Direct Memory Access (DMA) of intra-cardiac electrogram 348 (IEGM) or sensed analog-to-digital converter 342 (ADC) sample or conversion rates similar to those described in U.S patent application Ser. Nos. 08/561,738 and 08/768,687 to Muhlenberg, and the like;

(7) Data bus activity. Examples include, but are not limited to, sensing activity along local bus 618 and/or 620 of Microcomputer Circuit 314 and/or Digital Controller Timer Circuit 332, or sensing activity along Data Communication Bus 330;

(8) Timed or "alarmed" wakeups. Examples include, but are not limited to, sensing a two-second interrupt for rate response calculation similar to that described in U.S. Pat. No. 5,052,388 to Sivula et al., sensing completion of a diagnostic enable window or sensing the gathering of diagnostic data similar to that described in U.S. Pat. No. 5,330,513 to Bennett et al.

As described above, the signals, input and/or outputs monitored by Data Monitor 600 are input to a data processing device such as Digital Controller Timer Circuit, Microcomputer 314 and/or Microprocessor 320. The data processing device of the present invention which is employed in conjunction with Data Monitor 600 may be any one or more of the foregoing data processing devices, or may be any other type of suitable data processing device such as another type of controller, another type of microcomputer, another type of microprocessor, a micro-controller, a Digital Signal Processor (DSP), and so on. That is, those skilled in the art will now appreciate readily that in the present invention Data Monitor 600 may be employed with any of a number of different suitable data processing devices not disclosed explicitly herein.

FIG. 19 illustrates one embodiment of the present invention where any one or more of an output of comparator 349 (which is also an input to Digital Controller Timer Circuit 332), an output of clock source 338, an output of supply voltage source 301, an output of Activity Sensor 352, and/or an output of RF Tx/Rx 336 are monitored by Data Monitor 600. Those skilled in the art will recognize immediately that myriad other embodiments of the present invention not shown explicitly herein fall within the scope of the present invention.

Figure 20:
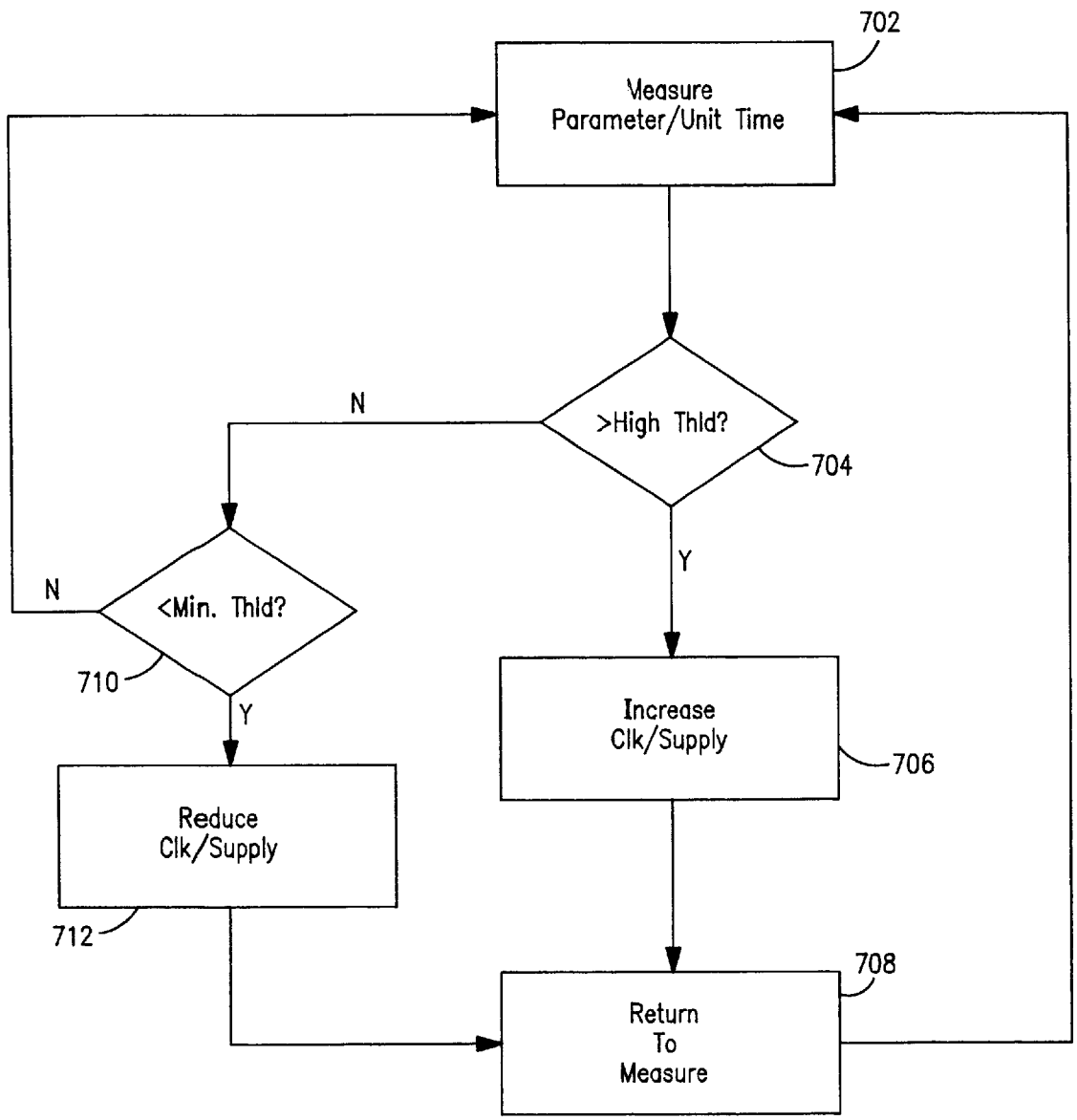
FIG. 20 shows one embodiment of a rate adaptive algorithm of the present invention.

Implementation of the present invention generally requires use of adaptive control algorithm 700, one example of which is shown in FIG. 20. The adaptive control algorithm should permit at least some operating parameters of circuit 300 to be adjusted "on the fly" on the basis of sensed signal inputs and/or outputs, or on the basis of sensed use or activity occurring in the circuitry to be monitored.

In preferred embodiments of the present invention, adaptive control algorithm 700 is capable of analyzing or reducing data, data patterns, and/or circuit activity levels, and on the basis of such data analysis or reduction adjusts the circuit or device's functionality or operation. For example, algorithm 700 may be employed to alter the functionality and delivery of power to the circuits and devices illustrated in FIGS. 9, 10 and 11. Examples of some the inputs to adaptive control algorithm 700 of the present invention are set forth immediately hereinabove in examples 1 through 8.

Data Monitor 600 in FIG. 19 measures or monitors data or signal activity, levels or characteristics such as signal amplitude, frequency and/or phase, and further most preferably employs algorithm 700 of FIG. 20. In addition to monitoring the inputs, outputs and signals described hereinabove, Data Monitor 600 also most preferably monitors data on various busses, such as data communication bus 330, internal local busses (not shown in FIG. 19) in microprocessor 320 via line 602, and digital controller timer circuit 332 via line 606. Data Monitor 600 may also monitor signal inputs to various circuits such as activity circuit 352 via line 608, RF Tx/Rx circuit 336 data via line 604, or sense amplifier output circuit 346 via line 610 connected to the output of sense amplifier comparator 349.

Note that in one general case Data or Signal Monitor 600 may monitor or sense signals or data anywhere between the points where input signals are initially brought into implantable medical device 300, and the points where inputs are fed into a data processing device such as Controller 620 or Microcomputer 314. Thus, Data or Signal Monitor 600 may monitor or sense signals or data before or after they have been subjected to preliminary or other signal conditioning, filtering, amplification or logic processing, but in any case before they are input to a central or principal data processing device such as Controller 332 or Microcomputer 314. In another general case, Data or Signal Monitor may monitor or sense signals or data anywhere along busses or other circuitry disposed between different data processing devices. For example, Data or Signal Monitor 600 may sense signals or data along bus 330 located between Controller 332 and Microcomputer 314.

Upon detection of predetermined signal levels or characteristics in the various lines, busses, circuits or sub-circuits monitored by Data or Signal Monitor 600, clock source 338 and/or system clock 322 are controlled via lines 616 or 614 to speed up or slow down. Additionally, Data Monitor 600 is capable of controlling supply voltage sources 612 and 301 via control lines 614 and 616, respectively, in response to sensing or detecting predetermined signal, amplitude, frequency, phase, voltage, current or logic levels or states in the various circuits or sub-circuits monitored thereby. Clocks 338 and 322 and voltage sources 612 and 301 are adjusted under the control of Data Monitor 600 to either minimize current drain while clock speed is decreased, or to allow optimum circuit function while clock speed is increased, all in a manner largely similar to that described hereinabove in respect of FIGS. 9, 10 and 11.

Data Monitor 600 may be any one or more of a microprocessor, a processor, a microcontroller, a controller, an Application Specific Integrated Circuit (ASIC), or may even be integrated into another, or form a portion of a, microprocessor, processor, microcontroller, controller and/ or Application Specific Integrated Circuit (ASIC) which performs at least some of the functions performed by microcomputer 31 and/or controller 332 in FIG. 19.

Referring now to FIG. 20, there is shown an exemplary algorithm 700 for controlling the functionality of Data Monitor 600 shown in FIG. 19. At block 702 a measurement is made of activity or signal transitions or changes occurring per unit time. The time period over which such measurements are made may be in milliseconds, seconds, minutes, hours or even days depending on the expected range of frequency of data arrival or generation. Block 704 periodically senses whether the activity measured in block 702 exceeds a predetermined level or threshold. That threshold may be fixed or programmable.

The rate at which block 704 senses activity will typically vary between milliseconds and minutes according to the particular signal, input or output being sensed, but may be longer. If the sensed signal exceeds the predetermined threshold (i.e., "yes"), then the controlled clock rate and/or the voltage supply's voltage will be increased at block 706 under the control of Data Monitor 600, and the algorithm will return to measure block 702 via block 708. If at block 704 the sensed result is "no", the minimum threshold is compared to the sensed signal at block 710. If the sensed signal is below the minimum threshold, the clock rate and/or the voltage supply's voltage is reduced at block 712 and a return to measure block 702 is effected via block 708. If at block 710 the result is "no", the algorithm returns to measure block 702.

Figure 21:
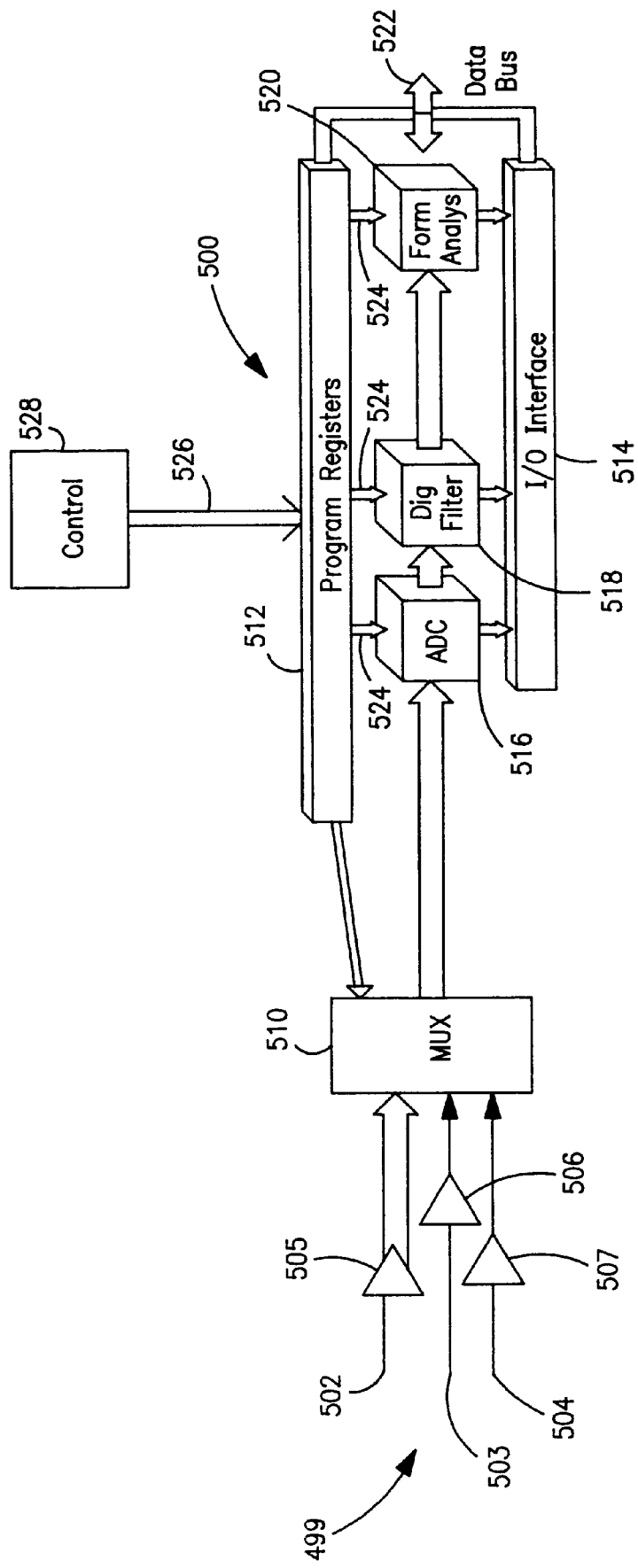
FIG. 21 shows a modified version of the schematic block diagram of FIG. 11 according to one embodiment of the present invention.

FIG. 21 shows a modification of the circuit shown in FIG. 11, where a DSP-based circuit is reconfigured by re-programming from an external programmer or alternatively under the active control of control circuit 528 in real time (or "on the fly"). Control circuit 528 is most preferably located inside implantable device 260. Monitor/control circuit 528 is most preferably programmed with or otherwise controls adaptive control algorithm 700 shown in FIG. 21 and typically monitors the same or similar signals, inputs and/or outputs described hereinabove. Busses 524 in FIG. 21 are most preferably capable of effecting reprogramming or reconfiguring of one or more of Mux 510, ADC 516, Digital Filter 518 and/or Form Analysis 520 to permit sensing and/or detection of a particular type of signal, input or output.

Such reconfiguration of DSP 500 permits adaptive filtering to be carried out which is based upon the particular type of signal, input or output being sensed. For example, DSP 500 may be programmed to discriminate between or to monitor for the occurrence of supraventricular tachycardia (SVT), atrial fibrillation (AF), atrial flutter (AFL), ventricular tachycardia (VT), ventricular fibrillation (VF), ventricular flutter (VFL), premature atrial contractions (PAC's), premature ventricular contractions (PVC's), signal-to-noise ratio (SNR, or the ratio of intrinsic cardiac signals to noise), electromagnetic interference (EMI), myopotentials, and so on.

Figure 22:
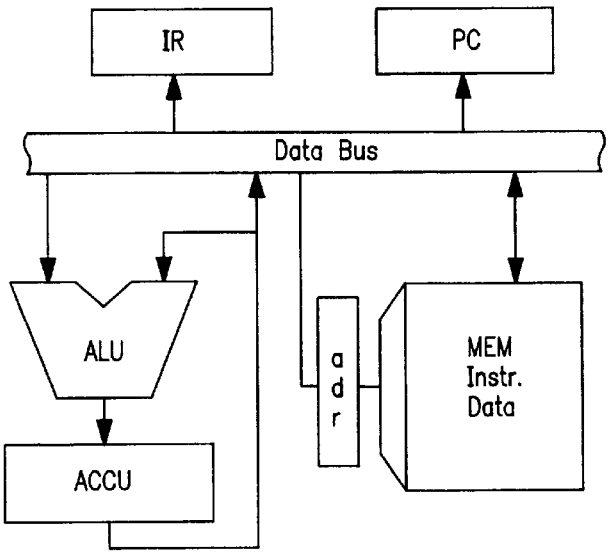
FIG. 22 shows conventional von Neumann microprocessor architecture.
Figure 23:
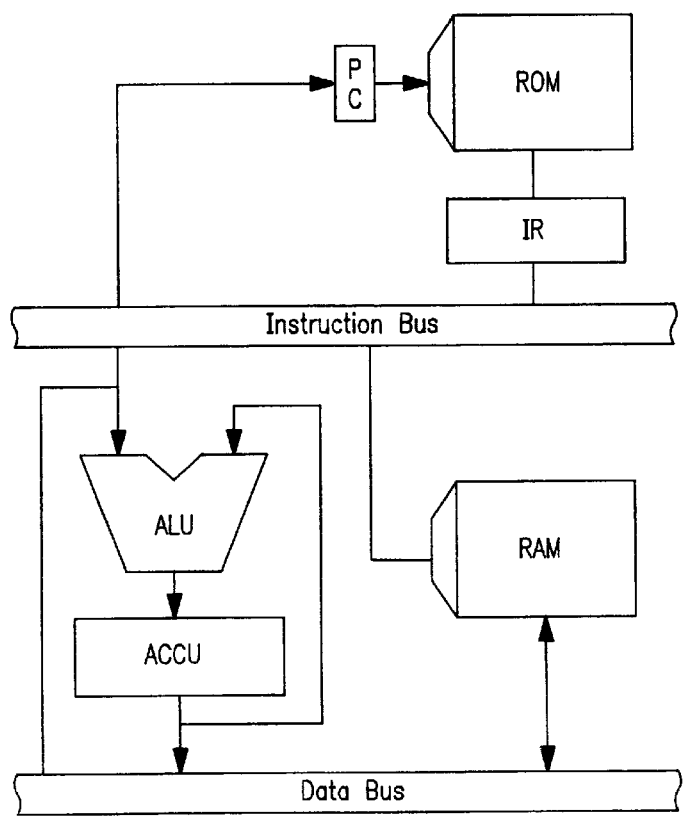
FIG. 23 shows one embodiment of Harvard microprocessor architecture of the present invention.

In yet another embodiment of the present invention, pipelining architecture is employed to reduce power consumption. Turning now to FIGS. 22 and 23, there are shown two principal types of microprocessor architectures:

the von Neumann architecture (shown in FIG. 22), and the Harvard architecture (shown in FIG. 23).

The von Neumann architecture of FIG. 22 generally has a single unified memory which stores both instructions and data. In the von Neumann architecture, a high throughput is required of the data bus. That is, all instructions, operand addresses and data must successively occupy the single bus.

In contrast, the Harvard architecture shown in FIG. 23 has two or more busses which permit instruction, address and data fetching to be done in parallel. The Harvard architecture typically has substantially greater processing throughput capability than does the von Neumann architecture. Consequently, the Harvard architecture is often employed in DSP's, where processing throughput demands are particularly high.

Two methods used to increase the effective processing speed or throughput of a microprocessor or DSP are: (1) to reduce the number of average clock cycles required to execute an instruction; and/or (2) to increase the clock speed (i.e., decrease the clock cycle length). One known method of reducing the average number of cycles required to execute an instruction without increasing the length of the clock cycle is to overlap the execution of multiple instructions. Such overlapping of instructions is known in the art as "pipelining".

Figure 24:
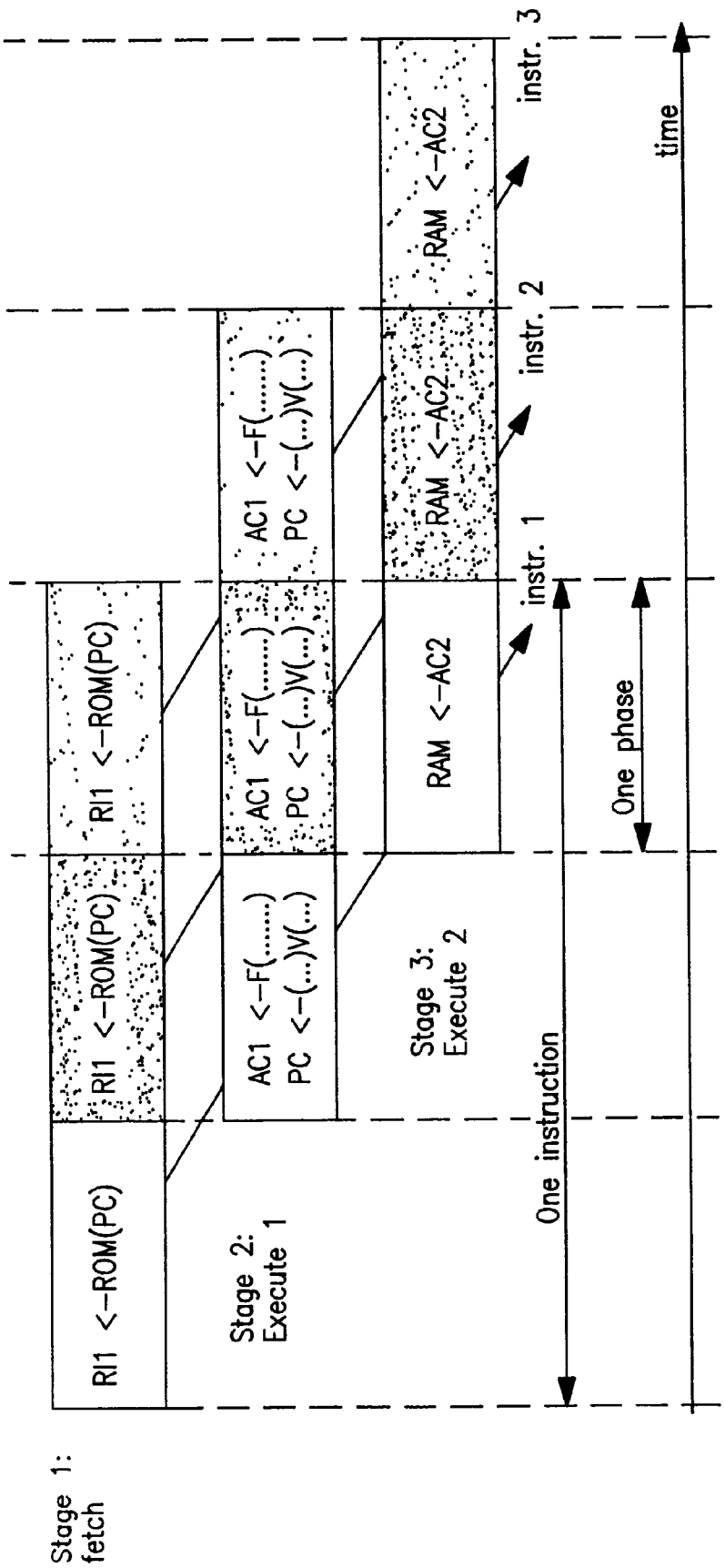
FIG. 24 shows one embodiment of a pipeline architecture timing diagram of the present invention.

Instruction pipelines function by dividing the execution of each instruction into several discrete portions, and then executing one portion of several different instructions simultaneously. As shown in FIG. 24, the execution of a single instruction can be subdivided into three discrete portions. FIG. 24 shows that each instruction is divided into three discrete portions or stages respectively labelled "Stage 1: fetch"; "Stage 2: Execute 1"; and "Stage 3: Execute 2." Three successive clock cycles are thus required to execute each complete instruction shown in FIG. 24. By creating such an instruction pipeline, a certain amount of operational or computational parallelism is achieved. Parallelism here signifies that three instructions are being executed simultaneously for any given clock cycle.

Continuing to refer to FIG. 24, it can be seen that during the clock cycle labelled "one phase", the third instruction (i.e., R|1→ROM(PC)) is initiated, the second instruction (i.e., AC1→F( . . . ) PC→( . . . )V( . . . )) is executed, and storing of the first instruction (RAM→AC2) is underway. Although each instruction still requires three clock cycles to execute, a three-level instruction pipeline like that illustrated in FIG. 24 results in a new instruction being initiated during each clock cycle.

When an instruction is being executed in each stage of the pipeline, the pipeline is said to be full. Once the pipeline is full, the effective rate of instruction completion is one instruction per clock cycle. By breaking down each instruction into three smaller and simpler discrete portions or parts, the individual parts may be executed faster, which in turn permits the individual clock cycles to be shortened. As the execution rate for new instructions depends upon the clock cycle, a shorter clock cycle leads to a higher instruction execution rate. Of course, maintaining this rate requires that the pipeline be kept full and that nothing delay the advance of instructions through the pipeline.

Figure 25:
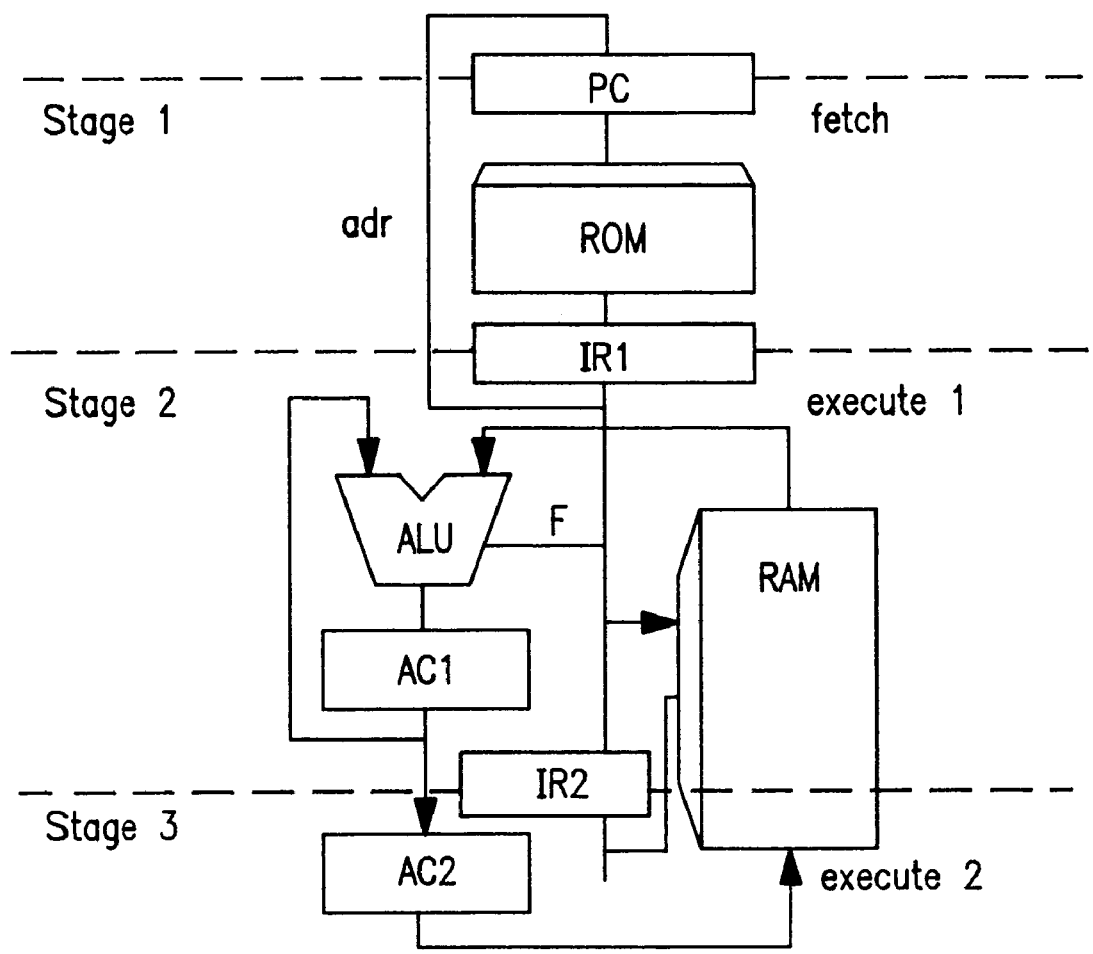
FIG. 25 shows one embodiment of pipeline architecture of the present invention.

FIG. 25 shows one embodiment of a microprocessor pipeline architecture finding application in the present invention having three stages and three phases for executing instructions. Each stage is designed to perform a specific phase of fetching or executing an instruction. Stage 1 is used to fetch an instruction from program memory and to load i in an instruction register. Stage 2 is used to execute an arithmetic logic unit (ALU) operation and to update a program counter. Stage 3 is used to load the result into data memory.

The prior art describing pipelining processors and pipeline architecture relates to increasing processing speed and computing power. See, for example, U.S. Pat. No. 5,187,796 to Wang entitled "Three-Dimensional Vector Co-Processor Having I, J and K Register Files and I, J and K Execution Units", hereby incorporated by reference herein in its entirety. See also U.S. Pat. No. 5,464,435 entitled "Parallel Processors in Implantable Medical Device" to Neumann, hereby incorporated by reference herein in its entirety, which describes using two processors in parallel in an implantable medical device to increase computational power.

Rather than seeking to increase the speed at which instructions at executed or to increase the number of calculations that can be made in a given unit of time, in the present invention, and completely contrary to the teachings of the prior art, a reduction in clock speed and pipelining architecture are employed in combination to reduce power consumption in medical and other devices. That is, instead of utilizing the two-, three-, four- or other-fold increase in speed or computing power gained by utilizing pipelining taught in the prior art, the present invention reduces clock speed the factor permitted by the particular pipeline architecture in question (e.g., clock speed is reduced by a factor of two, three, four or other factor), while processing capabilities roughly similar to those that would obtain if the pipeline architecture were not present or utilized are maintained. The reduction of clock speed in the present invention permits a reduction in the voltage of the voltage supply (VDD) provided. As a result, the capacity or current drain required of a battery powering an implantable medical device is reduced by the square of the resulting voltage difference in accordance with the teachings set forth hereinabove.

Those skilled in the art will now recognize that the technique of applying a lower supply voltage to digital circuitry of a device having a relatively large charged pumped voltage applied to the analog circuitry thereof may be applicable to other medical or implantable devices in a manner similar to that described in reference to a pacemaker. Application of different voltages to the analog and digital circuitry of the PCD described hereinabove in respect of FIG. 10, for example, may be employed to reduce power consumption.

Additionally, as power consumption is reduced in accordance with the present invention, further functionality may be added to a device such that the device has added functionality and yet lower or the same power consumption relative to a conventional prior art device.

A processor such as a DSP, microprocessor, microcontroller or controller in accordance with the present invention may perform, for example, various morphology detection functions in sensed and/or stored electrograms (EGM's), such as differentiation of retrograde P-waves from antegrade P-waves; differentiation of P-waves from far field R-waves (FFRW); differentiation of atrial fibrillation (AF) or atrial flutter (AFL) from sinus tachycardia (ST); differentiation of ventricular tachycardia (VT) or ventricular flutter (VFL) from supraventricular tachycardia (SVT); differentiation of cardiac signals from electromagnetic interference; and so on. U.S. Pat. No. 5,447,519 to Peterson entitled "Method and Apparatus for Discriminating Monophasic and Polyphasic Arrhythmias and for Treatment Thereof", hereby incorporated by reference herein in its entirety, describes methods and apparatus for discriminating between different types of cardiac signals which find application in the present invention. All patents referenced in the '519 patent to Peterson are also incorporated by referenced herein, each in its respective entirety.

Other adaptive filtering techniques, methods and apparatus also find application in the present invention, such as those described in U.S. Pat. No. 5,755,739 entitled "Adaptive and Morphological System for Discriminating P-Waves and R-Waves Inside the Human Body" to Sun et al.; U.S. Pat. No. 5,778,881 entitled "Method and Apparatus for Discriminating P and R Waves" to Sun et al.; U.S. Pat. No. 5,730,142 entitled "Method and Apparatus for Detecting Tachycardia" to Sun et al.; and U.S. Pat. No. 5,782,888 entitled "Method of Selecting an Operating Mode for an Implantable Medical Device" to Sun et. al., all hereby incorporated by reference herein, each in its respective entirety. All patents referenced in the foregoing '739, '881, '142 and '888 patents to Sun et al. are also incorporated by referenced herein, each in its respective entirety.

Also by way of example, various embodiments of the present invention may also be employed to detect or filter out electromagnetic interference (EMI) emanating from or generated by theft detectors, conductive signals, RF noise, myopotentials, and the like.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of any particular digital or analog circuits. Furthermore, the voltages applied need not be at any predefined level, but only need be different. Although a charge pump is preferred for generating the higher supply voltage described herein, there may be other voltage generation devices capable of generating the desired voltage levels for application to analog circuits.

The present invention is also not limited to use in conjunction with pacemakers or PCD's, but may find further application in other relevant areas such as personal computing or telecommunications where low power consumption is desired. The present invention further includes within its scope the use of other techniques described herein in conjunction with the application of different supply voltages to analog and digital circuits (such as, for example, just-in-time clocking devices and methods).

The present invention is also not limited, for example, to the use of only two DSP systems, and DSP systems in accordance with the present invention may be used with other clock frequency management techniques described herein (such as multiple clock frequencies for more than one function performed by one or more processors). Moreover, the supply voltage source used for the multiple DSP systems of the present invention may include not only discrete supply voltages, but may also include a source that is varied continuously over a particular range of voltages such as by a voltage regulator, with such voltages changed "on the fly" with corresponding clock frequencies. The present invention further includes within its scope methods of making and using the features, concepts and circuitry described hereinabove.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination.

I claim:

1. A medical device, comprising:
   at least one circuit operable to perform at least one function and having at least one of a first input and a first output connected thereto for receiving or outputting, respectively, a first input signal or a first output signal;

a power source for applying a first fixed supply voltage to at least first portions of the at least one circuit;

a voltage generation circuit having the first fixed supply voltage supplied thereto, the voltage generation circuit generating at least a second fixed supply voltage for application to at least second portions of the at least one circuit, the second fixed supply voltage being different from the first fixed supply voltage;

a processing device having a second input for receiving at least one of the first input signal and the first output signal, the first input signal or first output signal being input to the second output before or after having been subjected to any one of preliminary signal conditioning, filtering, amplification and logic processing, and a monitor circuit connected between the second input and the first input or first output, the monitor circuit being operable to at least one of measure, sense and detect at least one predetermined characteristic of the first input signal or the first output signal, the monitor circuit being connected to the voltage generation circuit and being operable, in response to measuring, sensing or detecting the at least one predetermined characteristic, to cause the voltage generation circuit to at least one of provide the second fixed supply voltage to the at least second portions of the at least one circuit and provide the first fixed supply voltage to the at least first portions of the at least one circuit.

2. The device of claim 1, wherein the second fixed supply voltage is greater than the first fixed supply voltage.

3. The device of claim 1, wherein the first fixed supply voltage is greater than the second fixed supply voltage.

4. The device of claim 1, wherein the at least one circuit further comprises one or more analog circuits operable to perform at least one function.

5. The device of claim 4, wherein the one or more analog circuits include at least one of an atrial sense amplifier, a ventricular sense amplifier, a T-wave amplifier, one or more bandpass filters, one or more detection circuits, one or more sensor amplification circuits, one or more physiological signal amplification circuits, one or more output circuits, a battery monitor circuit, and a power on reset circuit.

6. The device of claim 4, wherein the one or more analog circuits include at least one amplifier circuit for amplifying the one or more analog signals.

7. The method of claim 1, wherein the at least one circuit further comprises one or more digital circuits operable to perform at least one function.

8. The device of claim 7, wherein the device further includes means for adjusting the back gate bias of at least one of the one or more digital circuits.

9. The device of claim 7, wherein the one or more digital circuits include at least one of a processor, a controller and a memory.

10. The device of claim 7, wherein the one or more digital circuits include at least one digital signal processor having the first supply voltage applied thereto receiving data representative of one or more analog signals.

11. The device of claim 1, wherein the voltage generation circuit is a charge pump circuit for generating the second fixed supply voltage based on the first fixed supply voltage.

12. The device of claim 1, wherein the first supply voltage ranges between about 0.8 volts and about 1.5 volts.

13. The device of claim 1, wherein the second supply voltage ranges between about +/−2.0 volts and about +/−3.0 volts.

14. The device of claim 1, wherein the at least one circuit further comprises one or more analog circuits, one or more digital circuits, and a level shifter to translate signals between the one or more analog circuits and the one or more digital circuits.

15. The device of claim 1, wherein the device is an hermetically sealed implantable medical device.

16. The device of claim 15, wherein the implantable medical device is selected from the group consisting of an implantable stimulator, an implantable nerve stimulator, an implantable pacemaker, an IPG, an implantable cardioverter, an implantable PCD, an implantable defibrillator, an implantable ICD and an implantable drug pump.

17. The device of claim 1, wherein the at least one circuit comprises circuitry of a type selected from the group consisting of a CMOS circuit, a CML circuit, an SOS circuit, an SOI circuit, a BICMOS circuit, a PMOS circuit and an NMOS circuits.

18. The device of claim 1, wherein the processing device is selected from the group consisting of a microprocessor, a microcomputer, a controller, a microcontroller, a digital signal processor, a CPU and an Application Specific Integrated Circuit (ASIC).

19. The device of claim 1, wherein the monitor circuit employs an adaptive control algorithm to determine whether or not a measured, sensed or detected signal meets the at least one predetermined characteristic.

20. The device of claim 19, wherein the at least one predetermined characteristic is defined in respect of at least one of the sign, polarity, slope, rate of change, amplitude, frequency and phase of the measured, sensed or detected signal.

21. The device of claim 1, wherein the first input or first output is selected from the group consisting of an output of a comparator, an output of a clock source, an output of a clock, an output of a supply voltage source, an output of an activity sensor, an output of a telemetry circuit, a sensing input from a pacing lead, and a sensing input from a defibrillating lead.

22. The device of claim 1, wherein the first input or first output is selected from the group consisting of sensed normal intrinsic sensed events, premature atrial contractions (PAC's), premature ventricular contractions (PVC's), atrial and/or ventricular tachycardia, atrial and/or ventricular flutter, atrial and/or ventricular fibrillation, noise, electromagnetic interference, muscle signals, far-field R-waves (FFRW), and antegrade or retrograde p-waves.

23. The device of claim 1, wherein the first input or first output is selected from the group consisting of sensed complete memory data dumps, sensed selected memory location uplinks, detected re-transmissions in a noisy environment, sensed telemetry distance, transmission power, receiver sensitivity, bit error rate (BER), and the amount of data telemetered or received.

24. The device of claim 1, wherein the first input or first output is selected from the group consisting of sampling rates, an activity rate response signal, a cardiac acceleration signal, and an oxygen saturation signal.

25. The device of claim 1, wherein the first input or first output is a sensed intra-circuit block activity per unit time.

26. The device of claim 1, wherein the first input or first output is selected from the group consisting of a sensed number of operand codes processed per unit time and a sensed type of operand codes processed per unit time.

27. The device of claim 1, wherein the first input or first output is selected from the group consisting of a sensed telemetry data format, a sensed telemetry data movement, a sensed Direct Memory Access (DMA) of an intra-cardiac electrogram, a sensed analog-to-digital converter sample rate, and a sensed analog-to-digital converter conversion rate.

28. The device of claim 1, wherein the first input or first output is selected from the group consisting of sensed activity along a bus, sensed activity within a controller, sensed activity within a microcontroller, sensed activity within a microprocessor, and sensed activity within a digital signal processor.

29. The device of claim 1, wherein the first input or first output is selected from the group consisting of a timed wakeup, an alarmed wakeup, a sensed interrupt for rate response calculation, a sensed completion of a diagnostic enable window, and a sensed acquisition of diagnostic data.

30. The device of claim 1, wherein the monitor circuit comprises a device selected from the group consisting of a microprocessor, a microcomputer, a controller, a microcontroller, a digital signal processor, a CPU, and an Application Specific Integrated Circuit (ASIC).

31. The device of claim 1, wherein the monitor circuit is operable to execute an adaptive control algorithm.

32. The device of claim 31, wherein the adaptive control algorithm permits at least some operating parameters of the medical device to be adjusted on the fly on the basis of the measured, sensed or detected first input or first output.

33. The device of claim 1, wherein the monitor circuit further measures, senses or detects data moving along at least one data bus.

34. The device of claim 1, wherein the monitor circuit is programmable.

35. The device of claim 1, wherein the monitor circuit is programmable with an adaptive control algorithm.

36. The device of claim 1, wherein the monitor circuit comprises a programmable digital signal processor capable of at least one of having and executing an adaptive control algorithm programmed therein.

37. The device of claim 36, wherein the digital signal processor is capable of carrying out adaptive filtering on the measured, sensed or detected first input or first output.

38. The device of claim 37, wherein the digital signal processor is programmable to be capable of discriminating between or detecting at least one of supraventricular tachycardia (SVT), atrial fibrillation (AF), atrial flutter (AFL), ventricular tachycardia (VT), ventricular fibrillation (VF), ventricular flutter (VFL), premature atrial contractions (PAC's), premature ventricular contractions (PVC's), signal-to-noise ratio of intrinsic cardiac signals, electromagnetic interference (EMI) and myopotentials.

39. The device of claim 1, further comprising a clock source for providing clock signals at a plurality of clock frequencies, the clock source being operatively connected to control the at least one circuit at a clock frequency such that substantially the entire predetermined time period is used to perform the at least one function, the function being completed just prior to the subsequent time period.

40. The device of claim 39, wherein the at least one circuit further comprises at least a first logic circuit for performing a first function and a second logic circuit for performing a second function, the first logic circuit being operable to perform the first function during a first predetermined time period and the second logic circuit being operable to perform the second function during a second predetermined time period, each of the first and second logic circuits being operated at a different clock frequency such that substantially the entire respective first and second predetermined time periods are used by the respective first and second logic circuits to perform the respective first and second functions.

41. The device of claim 40, wherein the first predetermined time period and the second predetermined time period are time periods based on physiological events.

42. The device of claim 41, wherein at least one of the first and second time periods is a time period associated with a cardiac event and is selected from the group consisting of a blanking interval, an upper rate interval, an escape interval, a refractory interval, and a pulse generator/programmer handshake.

43. The device of claim 39, wherein the processing device is operable to perform a plurality of functions, each of the plurality of functions being performed during an associated predetermined time period prior to a subsequent time period in which another of the plurality of functions is performed, the processing device being operable to perform each of two or more functions of the plurality of functions at a different clock frequency such that substantially the entire associated predetermined time period for each function is used to perform the functions prior to the subsequent time period in which another of the plurality of functions is performed.

44. The device of claim 43, wherein the associated predetermined time periods are time periods based on physiological events.

45. The device of claim 43, wherein at least one of the associated time periods is a time period associated with a cardiac event and is selected from the group consisting of a blanking interval, an upper rate interval, an escape interval, a refractory interval, and a pulse generator/programmer handshake.

46. The device of claim 39, wherein the first and second voltages are applied to the first and second portions of the at least one circuit as a function of the clock frequency applied to the at least one circuit.

47. The device of claim 46, wherein the at least one circuit comprises at least a first logic circuit for performing a first function and a second logic circuit for performing a second function, wherein each of the first and second logic circuits is operated at a different clock frequency, and further wherein the first and second logic circuits have the first and second supply voltages applied thereto, respectively, based on the different clock frequencies used to control the first and second logic circuits.

48. The device of claim 39, wherein the processing device is operable to perform a plurality of functions, each of at least two of the plurality of functions is performed at a different clock frequency, and the supply voltage applied to the processing device by the one or more voltage sources is adjusted such that the first supply voltage is provided to the processing device during performance of one of the at least two functions and a second supply voltage is provided to the processing device during performance of the other function, wherein the first and second supply voltages are applied to the processing device based on the different clock frequencies used to control the processing device.

49. The device of claim 1, wherein the device further comprises:
   a multiplexer for receiving a plurality of analog signals; and
   an analog to digital converter for converting one or more of the analog signals to digital signals and applying such digital signals to the processing device.

50. A method of conserving power in a medical device, comprising:
   providing at least one circuit operable to perform at least one function and having at least one of a first input and a first output connected thereto for receiving or outputting, respectively, a first input signal or a first output signal;
   providing a power source for applying a first fixed supply voltage to at least first portions of the at least one circuit;

providing a voltage generation circuit having the first fixed supply voltage supplied thereto, the voltage generation circuit generating at least a second fixed supply voltage for application to at least second portions of the at least one circuit, the second fixed supply voltage being different from the first fixed supply voltage;

providing a processing device having a second input for receiving at least one of the first input signal and the first output signal, the first input signal or first output signal being input to the second output before or after having been subjected to any one of preliminary signal conditioning, filtering, amplification and logic processing, and providing a monitor circuit connected between the second input and the first input or first output, the monitor circuit being operable to at least one of measure, sense and detect at least one predetermined characteristic of the first input signal or the first output signal, the monitor circuit being connected to the voltage generation circuit and being operable, in response to measuring, sensing or detecting the at least one predetermined characteristic, to cause the voltage generation circuit to at least one of provide the second fixed supply voltage to the at least second portions of the at least one circuit and provide the first fixed supply voltage to the at least first portions of the at least one circuit.

51. The method of claim 50, wherein providing the at least one circuit further comprises providing one or more analog circuits operable to perform at least one function.

52. The method of claim 51, wherein providing the one or more analog circuits further comprises providing at least one of an atrial sense amplifier, a ventricular sense amplifier, a T-wave amplifier, one or more bandpass filters, is one or more detection circuits, one or more sensor amplification circuits, one or more physiological signal amplification circuits, one or more output circuits, a battery monitor circuit, and a power on reset circuit.

53. The method of claim 51, wherein providing the one or more analog circuits further comprises providing at least one amplifier circuit for amplifying the one or more analog signals.

54. The method of claim 50, wherein providing the at least one circuit further comprises providing one or more digital circuits operable to perform at least one function.

55. The method of claim 54, wherein providing one or more digital circuits further comprises providing means for adjusting the back gate bias of at least one of the one or more digital circuits.

56. The method of claim 54, wherein providing one or more digital circuits further comprises providing at least one of a processor, a controller and a memory.

57. The method of claim 54, wherein providing one or more digital circuits further comprises providing at least one digital signal processor having the first supply voltage applied thereto for receiving data representative of one or more analog signals.

58. The method of claim 50, wherein providing the voltage generation circuit further comprises providing a charge pump circuit for generating the second fixed supply voltage based on the first fixed supply voltage.

59. The method of claim 50, wherein providing the first supply voltage further comprises providing a voltage ranging between about 0.8 volts and about 1.5 volts.

60. The method of claim 50, wherein providing the second supply voltage further comprises providing a voltage ranging between about +/−2.0 volts and about +/−3.0 volts.

61. The method of claim 50, wherein providing the at least one circuit further comprises providing one or more analog circuits, one or more digital circuits, and a level shifter to translate signals between the one or more analog circuits and the one or more digital circuits.

62. The method of claim 50, further comprising hermetically sealing the medical device.

63. The method of claim 50, further comprising making the medical device an implantable medical device selected from the group consisting of an implantable stimulator, an implantable nerve stimulator, an implantable pacemaker, an IPG, an implantable cardioverter, an implantable PCD, an implantable defibrillator, an implantable ICD and an implantable drug pump.

64. The method of claim 50, wherein providing the at least one circuit comprises providing circuitry of a type selected from the group consisting of a CMOS circuit, a CML circuit, an SOS circuit, an SOI circuit, a BICMOS circuit, a PMOS circuit and an NMOS circuit.

65. The method of claim 50, wherein providing the monitor circuit further comprises providing an adaptive control algorithm for operation therein or therewith to determine whether or not a measured, sensed or detected signal meets the predetermined characteristics.

66. The method of claim 50, wherein the at least one predetermined characteristic is defined in respect of at least one of the sign, polarity, slope, rate of change, amplitude, frequency and phase of the measured, sensed or detected signal.

67. The method of claim 50, wherein providing the first input or first output further comprises providing at least one of an output of a comparator, an output of a clock source, an output of a clock, an output of a supply voltage source, an output of an activity sensor, an output of a telemetry circuit, a sensing input from a pacing lead, and a sensing input from a defibrillating lead.

68. The method of claim 50, wherein providing the first input or first output further comprises providing at least one of sensed normal intrinsic sensed events, premature atrial contractions (PAC's), premature ventricular contractions (PVC's), atrial and/or ventricular tachycardia, atrial and/or ventricular flutter, atrial and/or ventricular fibrillation, noise, electromagnetic interference, muscle signals, far-field R-waves (FFRW), and antegrade or retrograde p-waves.

69. The method of claim 50, wherein providing the first input or first output further comprises providing at least one of sensed complete memory data dumps, sensed selected memory location uplinks, detected re-transmissions in a noisy environment, sensed telemetry distance, transmission power, receiver sensitivity, bit error rate (BER), and the amount of data telemetered or received.

70. The method of claim 50, wherein providing the first input or first output further comprises providing at least one of a sampling rate, an activity rate response signal, a cardiac acceleration signal, and an oxygen saturation signal.

71. The method of claim 50, wherein providing the first input or first output further comprises providing sensed intra-circuit block activity per unit time.

72. The method of claim 50, wherein providing the first input or first output further comprises providing at least one of a sensed number of operand codes processed per unit time and a sensed type of operand codes processed per unit time.

73. The method of claim 50, wherein providing the first input or first output further comprises providing at least one of sensed telemetry data format, sensed telemetry data movement, sensed Direct Memory Access (DMA) of an intra-cardiac electrogram, sensed analog-to-digital converter sample rate, and sensed analog-to-digital converter conversion rate.

74. The method of claim 50, wherein providing the first input or first output further comprises providing at least one of sensed activity along a bus, sensed activity within a controller, sensed activity within a microcontroller sensed activity within a microprocessor, and sensed activity within a digital signal processor.

75. The method of claim 50, wherein providing the first input or first output further comprises providing at least one of a timed wakeup, an alarmed wakeup, a sensed interrupt for rate response calculation, a sensed completion of a diagnostic enable window, and a sensed acquisition of diagnostic data.

76. The method of claim 50, wherein providing the processing device further comprises providing at least one of a microprocessor, a microcomputer, a controller, a microcontroller, a digital signal processor, a CPU and an Application Specific Integrated Circuit (ASIC).

77. The method of claim 50, wherein the monitor circuit comprises a device selected from the group consisting of a microprocessor, a microcomputer, a controller, a microcontroller, a digital signal processor, a CPU, and an Application Specific Integrated Circuit (ASIC).

78. The method of claim 50, wherein providing the monitor circuit further comprises providing an adaptive control algorithm for execution thereby.

79. The method of claim 78, wherein providing the adaptive control algorithm further comprises providing the program to permit at least some operating parameters of the medical device to be adjusted on the fly on the basis of the measured, sensed or detected first input or first output.

80. The method of claim 50, wherein the monitor circuit further measures, senses or detects data moving along at least one data bus.

81. The method of claim 50, further comprising programming the monitor circuit.

82. The method of claim 50, further comprising programming the monitor with an adaptive control algorithm.

83. The method of claim 50, wherein providing the monitor circuit further comprises providing a programmable digital signal processor capable of having an adaptive control algorithm programmed therein.

84. The method of claim 83, wherein the digital signal processor is further capable of carrying out adaptive filtering on the measured, sensed or detected first input or first output.

85. The method of claim 83, wherein the digital signal processor is programmable to be capable of discriminating between or detecting at least one of supraventricular tachycardia (SVT), atrial fibrillation (AF), atrial flutter (AFL), ventricular tachycardia (VT), ventricular fibrillation (VF), ventricular flutter (VFL), premature atrial contractions (PAC's), premature ventricular contractions (PVC's), signal-to-noise ratio of intrinsic cardiac signals, electromagnetic interference (EMI) and myopotentials.

86. The method of claim 50, further comprising providing a clock source for providing clock signals at a plurality of clock frequencies, the clock source being operatively connected to control the at least one circuit at a clock frequency such that substantially the entire predetermined time period is used to perform the at least one function, the function being completed just prior to the subsequent time period.

87. The method of claim 86, wherein providing the at least one circuit further comprises providing at least a first logic circuit for performing a first function and providing a second logic circuit for performing a second function, the first logic circuit being operable to perform the first function during a first predetermined time period and the second logic circuit being operable to perform the second function during a second predetermined time period, each of the first and second logic circuits being operated at a different clock frequency such that substantially the entire respective first and second predetermined time periods are used by the respective first and second logic circuits to perform the respective first and second functions.

88. The method of claim 87, wherein the first predetermined time period and the second predetermined time period are time periods based on physiological events.

89. The method of claim 88, wherein at least one of the first and second time periods is a time period associated with a cardiac event and is selected from the group consisting of a blanking interval, an upper rate interval, an escape interval, a refractory interval, and a pulse generator/programmer handshake.

90. The method of claim 50, wherein the processing device is operable to perform a plurality of functions, each of the plurality of functions being performed during an associated predetermined time period prior to a subsequent time period in which another of the plurality of functions is performed, the processing device being operable to perform each of two or more functions of the plurality of functions at a different clock frequency such that substantially the entire associated predetermined time period for each function is used to perform the functions prior to the subsequent time period in which another of the plurality of functions is performed.

91. The method of claim 90, wherein the associated predetermined time periods are time periods based on physiological events.

92. The method of claim 91, wherein at least one of the associated time periods is a time period associated with a cardiac event and is selected from the group consisting of a blanking interval, an upper rate interval, an escape interval, a refractory interval, and a pulse generator/programmer handshake.

93. The method of claim 50, wherein the first and second voltages are applied to the first and second portions of the at least one circuit as a function of the clock frequency applied to the at least one circuit.

94. The method of claim 93, wherein providing the at least one circuit comprises providing at least a first logic circuit for performing a first function and providing a second logic circuit for performing a second function, wherein each of the first and second logic circuits is operated at a different clock frequency, and further wherein the first and second logic circuits have the first and second supply voltages applied thereto, respectively, based on the different clock frequencies used to control the first and second logic circuits.

95. The method of claim 50, wherein the processing device is operable to perform a plurality of functions, each of at least two of the plurality of functions is performed at a different clock frequency, and the supply voltage applied to the processing device by the one or more voltage sources is adjusted such that the first supply voltage is provided to the processing device during performance of one of the at least two functions and a second supply voltage is provided to the processing device during performance of the other function, wherein the first and second supply voltages are applied to the processing device based on the different clock frequencies used to control the processing device.

96. The method of claim 50, further comprising:
providing a multiplexer for receiving a plurality of analog signals; and
providing an analog to digital converter for converting one or more of the analog signals to digital signals and applying such digital signals to the processing device.

* * * * *

UNITED STATES PATENT AND TRADEMARK OFFICE
CERTIFICATE OF CORRECTION

PATENT NO. : 6,185,454 B1
DATED : February 6, 2001
INVENTOR(S) : David L. Thompson It is certified that error appears in the above-identified patent and that said Letters Patent is hereby corrected as shown below:

Column 37,
Line 32, "T-wave amplifier, one or more bandpass filters, is one or more detection circuits" should read "T-wave amplifier, one or more bandpass filters, -- one or more - detection circuits".

Signed and Sealed this

Fifteenth Day of January, 2002

Attest:

JAMES E. ROGAN
Director of the United States Patent and Trademark Office

Attesting Officer